United States Patent
Sun et al.

(10) Patent No.: US 11,291,657 B2
(45) Date of Patent: *Apr. 5, 2022

(54) METHODS OF TREATING INFLAMMATORY BOWEL DISEASE WITH AMD3100 AND TACROLIMUS

(71) Applicant: MedRegen, LLC, Baltimore, MD (US)

(72) Inventors: Zhaoli Sun, Perry Hall, MD (US); Xuhang Li, Clarksville, MD (US)

(73) Assignee: Medregen, LLC, Baltimore, MD (US)

( * ) Notice: Subject to any disclaimer, the term of this patent is extended or adjusted under 35 U.S.C. 154(b) by 95 days.

This patent is subject to a terminal disclaimer.

(21) Appl. No.: 16/540,985

(22) Filed: Aug. 14, 2019

(65) Prior Publication Data
US 2020/0038381 A1 Feb. 6, 2020

Related U.S. Application Data

(63) Continuation of application No. 14/814,988, filed on Jul. 31, 2015, now Pat. No. 10,420,751, which is a continuation-in-part of application No. 13/515,143, filed as application No. PCT/US2010/059877 on Dec. 10, 2010, now Pat. No. 10,813,917.

(60) Provisional application No. 61/384,017, filed on Sep. 17, 2010, provisional application No. 61/383,975, filed on Sep. 17, 2010, provisional application No. 61/316,180, filed on Mar. 22, 2010, provisional application No. 61/285,602, filed on Dec. 11, 2009.

(51) Int. Cl.
| | |
|---|---|
| A61K 31/436 | (2006.01) |
| A61K 38/13 | (2006.01) |
| A61K 31/395 | (2006.01) |
| A61K 45/06 | (2006.01) |
| A61K 31/00 | (2006.01) |
| A61K 38/19 | (2006.01) |

(52) U.S. Cl.
CPC ............ *A61K 31/436* (2013.01); *A61K 31/00* (2013.01); *A61K 31/395* (2013.01); *A61K 38/13* (2013.01); *A61K 38/193* (2013.01); *A61K 45/06* (2013.01)

(58) Field of Classification Search
None
See application file for complete search history.

(56) References Cited

U.S. PATENT DOCUMENTS

| | | | |
|---|---|---|---|
| 5,688,824 A | 11/1997 | Williams | |
| 10,420,751 B2 * | 9/2019 | Sun ..................... | A61K 45/06 |
| 2005/0271661 A1 | 12/2005 | Manivasakam et al. | |
| 2006/0211725 A1 | 9/2006 | Kobayashi et al. | |
| 2007/0190023 A1 | 8/2007 | Battista et al. | |
| 2008/0009495 A1 | 1/2008 | Kokubo et al. | |
| 2008/0038269 A1 | 2/2008 | Susan | |
| 2009/0325906 A1 | 12/2009 | Robbins et al. | |
| 2010/0105717 A1 | 4/2010 | Gordon et al. | |
| 2010/0226894 A1 | 9/2010 | Yeung et al. | |
| 2010/0303766 A1 | 12/2010 | Miyaji et al. | |
| 2013/0052231 A1 | 2/2013 | Sun et al. | |
| 2013/0108579 A1 | 5/2013 | Chen | |
| 2013/0202553 A1 | 8/2013 | Zheng | |

FOREIGN PATENT DOCUMENTS

| | | |
|---|---|---|
| EP | 0607775 A2 | 7/1994 |
| WO | 01/94420 A1 | 12/2001 |
| WO | 2005/039595 A1 | 5/2005 |
| WO | 2009/037093 A1 | 3/2009 |
| WO | 2009/074807 A2 | 6/2009 |
| WO | 2009/094456 A2 | 7/2009 |
| WO | 2010/022017 A2 | 2/2010 |
| WO | 2010/029185 A1 | 3/2010 |
| WO | 2010/054271 A1 | 5/2010 |
| WO | 2010/093802 A1 | 8/2010 |

OTHER PUBLICATIONS

Okabayashi, Takehiro et al., "Mobilization of Host Stem Cells Enables Long Term Liver Transplant Acceptance in a Strongly Rejecting Rat Strain Combination", *Am J Transplant* Oct. 2011; 11(10); pp. 2046-2056, doi: 10.1111/j1600-6143.2011.03698.x.

Hu, Xiaopeng et al., "Chimeric Allografts Induced by Short-Term Treatment with Stem Cell Mobilizing Agents Result in Long-term Kidney Transplant Survival without Immunosuppression: I, Study in Rats", *Am J Transplant* Jul. 2016, 16(7): pp. 2055-2065, doi:10.1111/ajt.13706.

Cameron, A.M. et al., "Chimeric Allografts Induced by Short-Term Treatment with Stem Cell Mobilizing Agents Result in Long-term Kidney Transplant Survival without Immunosuppression: II, Study in Miniature Swine", *American Journal of Transplantation 2016*, 16: pp. 2066-2076, doi10.1111/ajt.13703.

Xia, Xian-Ming et al., "CXCR4 Antagonist AMD3100 Modulates Claudin Expression and Intestinal Barrier Function in Experimental Colitis", *PLoS ONE*, vol. 6, Issue 11, Nov. 2011, pp. 1-11.

Xia, Xian-Ming et al., "CXCR4 Antagonist AMD3100 Attenuates Colonic Damage in Mice with Experimental Colitis", World Journal of Gastroenterology, vol. 16, Issue 23, Jun. 21, 2010, pp. 2873-2880.

Thin, Lena W.Y., et al., "Oral Tacrolimus for the Treatment of Refractory Inflammatory Bowel Disease in the Biologic Era", *Inflamm Bowel Dis*, vol. 19, No. 7, Jun. 2013, pp. 1490-1498.

(Continued)

*Primary Examiner* — Phillip Gambel
(74) *Attorney, Agent, or Firm* — DLA Piper LLP (US)

(57) ABSTRACT

The present invention relates to the field of inflammatory bowel disease. In one aspect, the present invention provides methods for treating inflammatory bowel disease in a patient comprising administering to the patient a therapeutically effective amount of a stem cell mobilizer and an immunosuppressive agent. In particular embodiments, the present invention provides a method for treating inflammatory bowel disease in a patient comprising administering to the patient a therapeutically effective amount of an agent that mobilizes $CD34^+$ and/or $CD133^+$ stem cells and a low dose of an immunosuppressive agent.

5 Claims, 26 Drawing Sheets

(56) References Cited

OTHER PUBLICATIONS

Marlicz, Wojciech et al., "Various Types of Stem Cells, Including a Population of Very Small Embryonic-Like Stem Cells, Are Mobilized into Peripheral Blood in Patients with Crohn's Disease", *Inflamm Bowel Dis*, vol. 18, No. 9, Jun. 2012, pp. 1711-1722.
Indriolo, Amedeo et al., "Clinical Management of Inflammatory Bowel Disease in the Organ Recipient", WGR 20th Anniversary Special Issues (3) *Inflammatory Bowel Disease, World Journal of Gastroenterology*, vol. 20, Issue 13, Apr. 7, 2014, pp. 3525-3533.
Tsuchiya, Atsunori et al., "Clinical Trials Using Mesenchymal Stem Cells in Liver Diseases and Inflammatory Bowel Diseases", BioMed Central, *Inflammation and Regeneration*, vol. 27, No. 16, 2017, pp. 1-15.
Werner, Lael et al., "Involvement of CXCR4/CXCR7/CXCL12 Interactions in Inflammatory Bowel Disease", *Theranostics*, vol. 3, Issue 1, 2013, pp. 40-46.
Renna, Sara et al., "Optimization of the Treatment with Immunosuppressants and Biologies in Inflammatory Bowel Disease", WGR 20th Anniversary Special Issues (3) Inflammatory Bowel Disease, *World Journal of Gastroenterology*, vol. 20, Issue 29, Aug. 7, 2014, pp. 9675-9690.
Kiesler et al., Cell Mol Gatroenterol Hepatol 1: 154-170, 2015.
Non-Final Office Action from corresponding U.S. Appl. No. 13/515,143, dated Sep. 25, 2017.
European Communication dated Mar. 14, 2016 from corresponding European Patent Application No. 10836746.7.
Muramatsu, K. et al., "Prolonged Survival of Experimental Extremity Allografts: A New Protocol with Total Body Irradiation, Granulocyte-Colony Stimulation Factor, and FK506", *Journal of Orthopaedic Research*, Jan. 1, 2009, pp. 457-461.
Margarit, C. et al., "Efficacy and safety of oral low-dose tacrolimus treatment in liver transplantation," *Transplant International*, vol. 11, No. Suppl. 1, Jun. 5, 1998, p. S260-S266.
Podesser, B.K., "Comparison of Low and High Initial Tacrolimus Dosing in Primary Heart Transplant Recipients: A Prospective European Multicenter Study", *Transplantation*, Vo. 79, No. 1, Jan. 15, 2005, pp. 65-71.
Davies, S.L., et al., "Plerixafor Hydrochloride," *Drugs of the Future*, vol. 32, No. 2, Jan. 1, 2007, p. 123.
Pento, J.T., "FK-506," *Drugs of the Future*, vol. 14, No. 8, Jan. 1, 1989, pp. 746-752.
Francavilla, A., et al., "Augmentation of rat liver regeneration by FK 506 compared with cyclosporin", *The Lancet*, 1248-1249, Nov. 25, 1989.
Tamura, F., et al., "FK506 promotes liver regeneration by suppressing natural killer cell activity", *Journal of Gastroenterology and Hepatology*, 13, 703-708 (1998).
Francavilla, A. et al., "Studies on mechanisms of augmentation of liver regeneration by cyclosporine and FK 506", Hepatology, 14(1) 140-143 (Jul. 1991).
Nishinaka, Y. et al., "Protective effect of FK506 on ischemia/reperfusion-induced myocardial damage in canine heart", Journal of Cardiovascular Pharmacology, 21(3), 448-454 (1993).
Sakr, M. et al., "FK 506 pre-treatment is associated with reduced levels of tumor necrosis factor and interleukin 6 following hepatic ischemia/reperfusion", Journal of Hepatology, 17: 301-307 (1993).
Van Thiel, D., et al., "FK 506 reduces the injury experienced following renal ischemia and reperfusion", Renal Failure, 14(3), 285-288 (1992).
Choi, H. et al., "Plerixafor for stem cell mobilization in patients with non-hodgkin's lymphoma and multiple myeloma", Annals of Pharmacotherapy, 44(1), 117-216(2010).
Extended European Search Report from corresponding European Patent Application No. 20211227.2 dated Jun. 21, 2021.
Partial Search Report from corresponding European Patent Application No. 20 211 227.2 dated Mar. 19, 2021.

\* cited by examiner

SDF-1 expression in Small Liver Grafts after Transplantation (DA into Lewis)

FIG. 24A
FIG. 24B
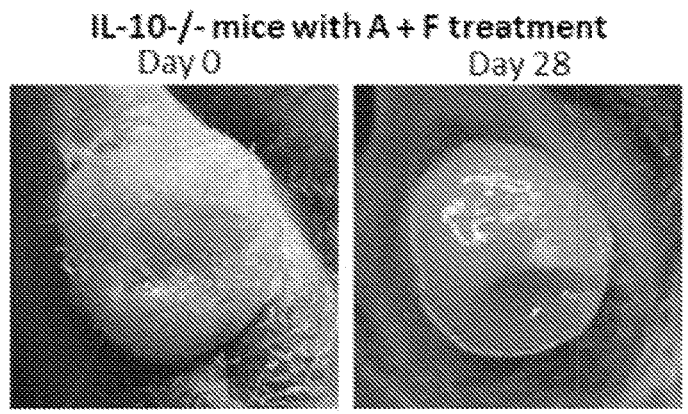
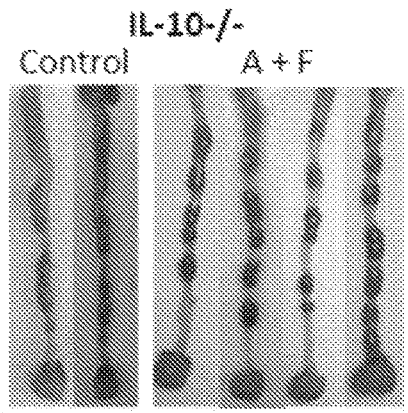
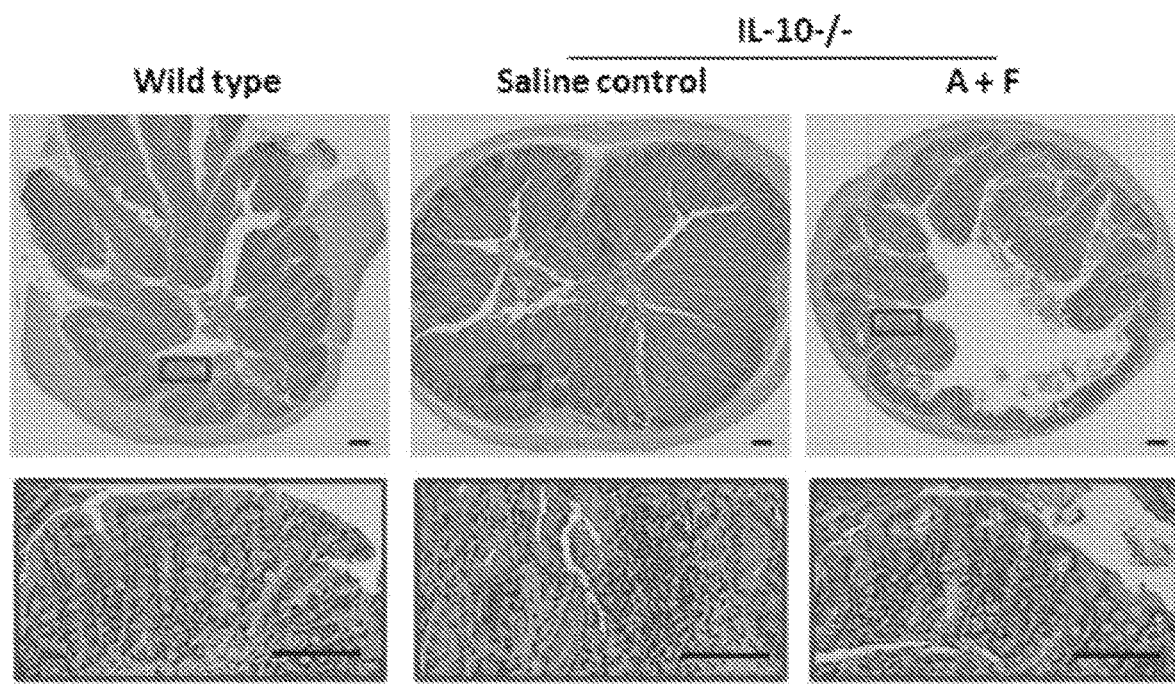
FIG. 24C

METHODS OF TREATING INFLAMMATORY BOWEL DISEASE WITH AMD3100 AND TACROLIMUS

STATEMENT OF GOVERNMENTAL INTEREST

This invention was made with U.S. government support under grant no. AI065488. The U.S. government has certain rights in the invention.

FIELD OF THE INVENTION

The present invention relates to the field of inflammatory bowel disease (IBD).

BACKGROUND OF THE INVENTION

As the early outcomes of human organ transplantation have dramatically improved, research focus has shifted toward solving the remaining problems associated with chronic immunosuppression. Calcineurin inhibitors remain the mainstay of immunosuppression in organ transplantation, but are associated with important side effects such as infections, diabetes, hypertension, nephrotoxicity and malignancy which can influence quality of life and survival rates. The ultimate goal of organ transplantation is to achieve clinical tolerance which is defined as stable normal graft function in the absence of immunosuppression.

SUMMARY OF THE INVENTION

The present invention is based, in part, on the discovery that the administration of a stem cell mobilizer in combination with an immunosuppressive agent can be used to treat organ transplant recipients. As described herein, the treatment regimen promotes allograft survival and induces long-term allograft acceptance. The treatment regimen can be applied to any type of organ transplant including liver, kidney, skin, heart, lung, intestine, and pancreas. The treatment regimen can also be applied to composite tissue transplantation. The composite tissue can be hand, face, or any other anatomical part. In particular embodiments, the treatment regimen can be utilized for toxic liver injury such as acetaminophen or fulminant hepatitis. In general, however, the present invention is useful in the treatment of patients with ischemic injury and/or shock.

Accordingly, in one embodiment, a method of treating an organ transplant recipient comprises administering to the recipient a therapeutically effective amount of a stem cell mobilizer and an immunosuppressive agent. The transplanted organ can be selected from the group consisting of liver, kidney, skin, heart, lung, intestine, and pancreas. In a specific embodiment, the organ is liver. In another embodiment, the organ is kidney. In yet another embodiment, the transplanted organ is skin.

In a more specific embodiment, a method of treating a liver transplant recipient comprises administering to the recipient a therapeutically effective amount of a stem cell mobilizer and an immunosuppressive agent. In another embodiment, a method of treating a kidney transplant recipient comprising administering to the recipient a therapeutically effective amount of a stem cell mobilizer and an immunosuppressive agent. In yet another embodiment, a method of treating a skin transplant recipient comprises administering to the recipient a therapeutically effective amount of a stem cell mobilizer and an immunosuppressive agent. In a further embodiment, a method of treating a patient diagnosed with ischemic injury comprises administering to the patient a therapeutically effective amount of a stem cell mobilizer and an immunosuppressive agent. In another specific embodiment, a method of treating a composite tissue transplant recipient comprises administering to the recipient a therapeutically effective amount of a stem cell mobilizer and an immunosuppressive agent.

The present invention further provides a method of treating an organ transplant recipient comprising administering to the recipient a therapeutically effective amount of an agent that mobilizes $CD34^+$ and/or $CD133^+$ stem cells and a low dose of an immunosuppressive agent. In particular embodiments, the agent that mobilizes $CD34^+$ and/or $CD133^+$ stem cells is AMD3100 and the immunosuppressive agent is Tacrolimus.

The present invention also provides a method of treating inflammatory bowel disease in a patient comprising administering to the patient a therapeutically effective amount of a stem cell mobilizer and an immunosuppressive agent. In another embodiment, a method of treating inflammatory bowel disease comprising in a patient administering to the patient a therapeutically effective amount of an agent that mobilizes $CD34^+$ and/or $CD133^+$ stem cells and a low dose of an immunosuppressive agent. IBD can include ulcerative colitis (UC), Crohn's disease (CD) and indeterminate colitis (IC).

The stem cell mobilizer can be any stem cell mobilizer including, but not limited to, AMD3100, AMD3465, TG-0054, G-CSF, GM-CSF, SDF-1, and SCF. In a specific embodiment, the stem cell mobilizer is a CXCR4 antagonist. In a more specific embodiment, the stem cell mobilizer is AMD3100.

The immunosuppressive agent can be any immunosuppressive agent including, but not limited to, Tacrolimus, cyclosporine, Orthoclone OKT3, mycophenolate, and sirolimus. In a specific embodiment, the immunosuppressive agent is Tacrolimus. In certain embodiments, the immunosuppressive agent is administered in a low dose amount.

In particular embodiments, the stem cell mobilizer is AMD3100 and the immunosuppressive agent is Tacrolimus. In other embodiments, the stem cell mobilizer and the immunosuppressive agent are the same compound.

BRIEF DESCRIPTION OF THE FIGURES

FIG. 5A: for small liver and FIG. 5B: for skin allograft.

FIG. 18A: 7 days after transplantation, FIG. 18B: 28 days after transplantation.

FIG. 21A: bloody and loose stools. FIG. 21B: shorter colon and enlarged cecum. FIG. 21C: H&E staining of colon. $*p<0.05$, n=4.

FIG. 24A-C. AF treatment decreased colonic inflammation in the IL-10-deficient murine model of IBD. FIG. 24A: rectal prolapse. FIG. 24B: Colon and stools. FIG. 24C: H&E staining of colon sections. Representative photographs of n=3 or 4 individual samples per group.

DETAILED DESCRIPTION OF THE INVENTION

Figure 1:
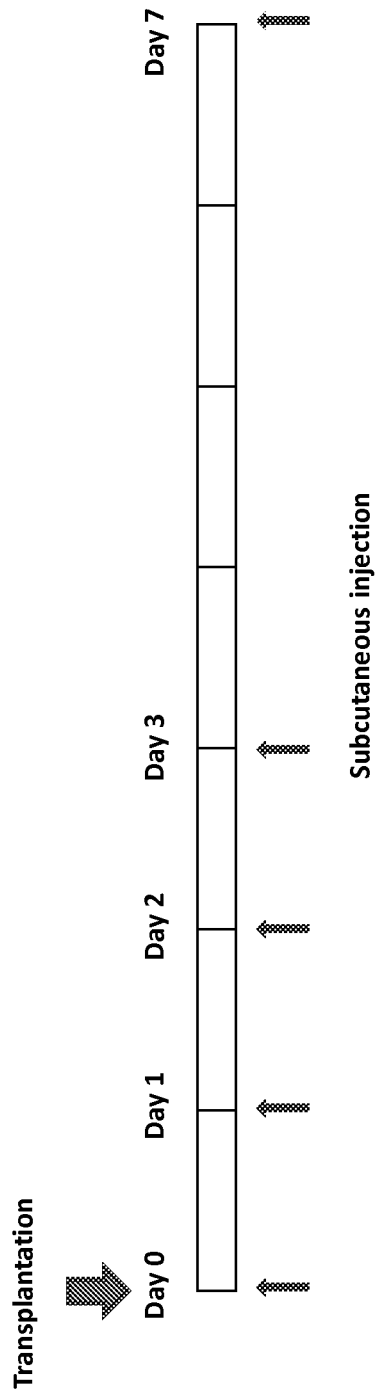
FIG. 1 presents the experimental protocol used for small liver transplantation.

It is understood that the present invention is not limited to the particular methods and components, etc., described herein, as these may vary. It is also to be understood that the terminology used herein is used for the purpose of describing particular embodiments only, and is not intended to limit the scope of the present invention. It must be noted that as used herein and in the appended claims, the singular forms "a," "an," and "the" include the plural reference unless the context clearly dictates otherwise. Thus, for example, a reference to a "protein" is a reference to one or more proteins, and includes equivalents thereof known to those skilled in the art and so forth.

Unless defined otherwise, all technical and scientific terms used herein have the same meaning as commonly understood by one of ordinary skill in the art to which this invention belongs. Specific methods, devices, and materials are described, although any methods and materials similar or equivalent to those described herein can be used in the practice or testing of the present invention.

All publications cited herein are hereby incorporated by reference including all journal articles, books, manuals, published patent applications, and issued patents. In addition, the meaning of certain terms and phrases employed in the specification, examples, and appended claims are provided. The definitions are not meant to be limiting in nature and serve to provide a clearer understanding of certain aspects of the present invention.

The present invention is based, in part, on the discovery that the administration of a stem cell mobilizer in combination with an immunosuppressive agent can be used to treat organ transplant recipients. As described herein, the treatment regimen promotes allograft survival and induces long-term allograft acceptance. The treatment regimen can be applied to any type of organ transplant including liver, kidney, skin, heart, lung, intestine, and pancreas. The treatment regimen can also be applied to composite tissue transplantation. The composite tissue can be hand, face, or any other anatomical part. In particular embodiments, the treatment regimen can be utilized for toxic liver injury such as acetaminophen or fulminent hepatitis. In general, however, the present invention is useful in the treatment of patients with ischemic injury and/or shock. Although much of the present disclosure is made in the context of organ transplantation, it should be recognized that the treatment regimens are broadly applicable, as noted above, and should not be construed as limited to organ transplantation.

The present invention consists of a novel strategy to mobilizer recipient stem cells which can promote the repair and regeneration of rejecting allografts after transplantation and eventually the allograft becomes recipient itself. This allows minimal immunosuppression and rapid weaning. For patients, this translates into improved survival and elimination of immunosuppression related complications, such as infections and malignancy.

In a chronic acceptance rat allogeneic liver transplant model, the inventors demonstrated that whole and partial donor livers are completely replaced by recipient-derived cells at 1 year and 3 months, respectively. The inventors have further demonstrated that recipient-derived hepatocytes result from cell transdifferentiation not cell fusion, and that these recipient-derived cells originate from bone marrow. These data suggest that the chimeric liver becomes increasingly like the recipient, and therefore, conveys tolerance.

As described herein, in an acute rejection rat liver transplantation model, the present inventors have further demonstrated that treatment of a liver transplant recipient with a stem cell mobilizer and an immunosuppressive agent facilitates a more rapid repopulation of liver allografts with recipient-derived cells after transplantation and induces long-term liver allograft acceptance without side effects.

The present inventors have also investigated the induction of kidney allograft acceptance, and have demonstrated herein that treatment with a combination of a stem cell mobilizer and an immunosuppressive agent prevents acute rejection and induces long-term allograft acceptance. As described in the Examples, kidney transplants from dark agouti (DA) rats to Lewis rats were performed and recipient rats were treated with stem cell mobilizer (mozobil: AMD3100) and/or low dose immunosuppressant (Tacrolimus, FK-506). Indeed, the present invention demonstrates that that stem cell mobilizers and immunosuppressive agents can be used for induction of kidney allograft acceptance (tolerance) and avoidance of chronic immunosuppression in organ transplantation.

The present invention is also useful in skin transplantation. According to the American Burn Association, there are approximately 500,000 burn injuries per year in the United States, with roughly 40,000 requiring hospitalization. Orgill et al., 360 N. ENGL. J. MED. 893-901 (2009). A treatment option that has helped to decrease mortality over the past ten years has been the immediate excision of burned skin with replacement by grafted skin. See Wang et al., 28 J. BURN CARE RES.182-86 (2007); Nakazawa et al., 106 NIPPON GEKA GAKKAI ZASSHI 745-49 (2005); and Desai et al., 211 ANN. SURG. 753-59 (1990). The ideal material for grafting is autologous skin, taken from a non-burned region of the patient's own skin. The supply of healthy autologous skin, however, is limited in severely burned patients, even when expansion techniques, such as "meshing," are used. See Lari et al., 27 BURNS 61-66 (2001); and Vandeput et al., 21 BURNS 364-70 (1995). Allogeneic skin is considered the gold standard for temporary grafts. Orgill et al., 360 N. ENGL. J. MED. 893-901 (2009).

The possibility of using allogenic skin and immunosuppression has been explored clinically and experimentally. An extensive burn injury is in itself immunosuppressive; nevertheless, the extreme antigenicity of skin inevitably results in the rejection of allograft. As in other allotransplants, attempts have been made to prolong the allograft acceptance by pharmacologically induced immunosuppression.

The agents most frequently used are cyclosporin and cyclosporin A. Black et al. reported on the use of cyclosporin-induced long-term allograft survival in 1987. 8 J. BURN CARE REHABIL. 531-35 (1987). This experimental work on rat models was further evaluated in the early 1990s. Cetinkale et al., 19 BURNS 262-64 (1993). An interesting observation in this later study was that the immunosuppressive effect of the burn injury was quickly reversed after early excision and grafting. This emphasizes the need for additional immunosuppression if burn wound cover with allograft alone is to be attempted.

The outcome of attempts to immunosuppress patients with large burns and allografts have on the whole been disappointing. While there are occasional reports of prolonged survival these are rare and more often the experience has been that patients succumb to sepsis possibly related to the immunosuppression.

Accordingly, the present invention further comprises methods to mobilize recipient stem cells which can promote the repair and regeneration of rejecting skin allografts after transplantation and eventually the allograft becomes recipient itself. This will allow minimal immunosuppression and rapid weaning. For burn patients, this would translate into improved survival and elimination of immunosuppression related complications, such as infections. Skin allograft may find a new role as a permanent skin in burn patients.

As further shown herein, the treatment regimen of the present invention recruits regulatory T-cells to the organ transplant site. Because regulatory T cells are involved in controlling autoimmune diseases including, but not limited to, type 1 diabetes, experimental autoimmune encephalomyelitis, and inflammatory bowel disease, the mobilization of stem cells (e.g., with a combination of AMD3100 and tacrolimus) may have broader clinical applications rather than transplantation. In particular embodiments, therefore, the stem cell mobilizers and immunosuppressive agents can be used to treat autoimmune disease.

I. Definitions

"Agent" refers to all materials that may be used as or in pharmaceutical compositions, or that may be compounds such as small synthetic or naturally derived organic compounds, nucleic acids, polypeptides, antibodies, fragments, isoforms, variants, or other materials that may be used independently for such purposes, all in accordance with the present invention.

"Antagonist" refers to an agent that down-regulates (e.g., suppresses or inhibits) at least one bioactivity of a protein. An antagonist may be a compound which inhibits or decreases the interaction between a protein and another molecule, e.g., a target peptide or enzyme substrate. An antagonist may also be a compound that down-regulates expression of a gene or which reduces the amount of expressed protein present.

"Hematopoiesis" refers to the highly orchestrated process of blood cell development and homeostasis. Prenatally, hematopoiesis occurs in the yolk sack, then liver, and eventually the bone marrow. In normal adults it occurs in bone marrow and lymphatic tissues. All blood cells develop from pluripotent stem cells. Pluripotent cells differentiate into stem cells that are committed to three, two or one hematopoietic differentiation pathway. None of these stem cells are morphologically distinguishable, however.

The term "immunosuppressive agent" refers to an agent that inhibits, slows or reverses the activity of the immune system. Immunosuppressive agents act by suppressing the function of responding immune cells (including, for example, T cells), directly (e.g., by acting on the immune cell) or indirectly (by acting on other mediating cells).

The terms "stem cells" and "hematopoietic stem cells" are used interchangeably herein. Stem cells are distinguished from other cell types by two important characteristics. First, stem cells are unspecialized cells capable of renewing themselves through cell division, sometimes after long periods of inactivity. Second, under certain physiologic or experimental conditions, stem cells can be induced to become tissue- or organ-specific cells with special functions. In some organs, such as the gut and bone marrow, stem cells regularly divide to repair and replace worn out or damaged tissues. In other organs, however, such as the pancreas and the heart, stem cells only divide under special conditions.

The term "stem cells" can refer to multipotent stem cells that are capable of differentiating into all blood cells including erythrocytes, leukocytes and platelets. For instance, the "hematopoietic stem cells" or "stem cells" as used in the invention are contained not only in bone marrow but also in umbilical cord blood derived cells.

A "stem cell mobilizer," "mobilizer of hematopoietic stem cells or progenitor cells" or "mobilize," (used interchangeably), as described herein, refers to any compound, whether it is a small organic molecule, synthetic or naturally derived, or a polypeptide, such as a growth factor or colony stimulating factor or an active fragment or mimic thereof, a nucleic acid, a carbohydrate, an antibody, or any other agent that acts to enhance the migration of stem cells from the bone marrow into the peripheral blood. A stem cell mobilizer may increase the number of hematopoietic stem cells or hematopoietic progenitor/precursor cells in the peripheral blood, thus allowing for a more accessible source of stem cells for use in transplantation. In particular embodiments, a stem cell mobilizer refers to any agent that mobilizes $CD34^+$ and/or $CD133^+$ stem cells. In other embodiments, a stem cell mobilizer disrupts CXCL12 (SDF-1)-mediated chemoattraction of CXCR4-expressing cells.

A "patient," "subject," "host," or "transplant recipient" to be treated by the present methods refers to either a human or non-human animal, such as primates, mammals, and vertebrates.

A "small molecule" refers to a composition that has a molecular weight of less than 3 about kilodaltons (kDa), less than about 1.5 kilodaltons, or less than about 1 kilodalton. Small molecules may be nucleic acids, peptides, polypeptides, peptidomimetics, carbohydrates, lipids or other organic (carbon-containing) or inorganic molecules. A "small organic molecule" is an organic compound (or organic compound complexed with an inorganic compound (e.g., metal)) that has a molecular weight of less than about 3 kilodaltons, less than about 1.5 kilodaltons, or less than about 1 kDa.

As used herein, the terms "treatment," "treating," "treat" and the like, refer to obtaining a desired pharmacologic and/or physiologic effect. The terms are also used in the context of the administration of a "therapeutically effective amount" of an agent, e.g., a stem cell mobilizer and/or an immunosuppressive agent. The effect may be prophylactic in terms of completely or partially preventing a particular outcome, disease or symptom thereof and/or may be therapeutic in terms of a partial or complete cure for a disease and/or adverse effect attributable to the disease. "Treatment," as used herein, covers any treatment of a disease in a subject, particularly in a human, and includes: (a) preventing the disease from occurring in a subject which may be predisposed to the disease but has not yet been diagnosed as having it; (b) inhibiting the disease, i.e., arresting its development; and (c) relieving the disease, e.g., causing regression of the disease, e.g., to completely or partially remove symptoms of the disease. In particular embodiments, the term is used in the context of treating organ transplant recipients. More particularly, treatment of an organ transplant recipient includes (a) achieving clinical tolerance; (b) promoting the repair and regeneration of rejecting allografts; (c) repopulating allografts with recipient-derived cells; (d) inducing long-term allograft acceptance without side effects; (e) reducing or eliminating immunosuppression related complications such as infections. In other embodiments, the term is used in the context of treating autoimmune diseases including IBD.

II. Stem Cell Mobilizers

The present invention relates to the treatment of organ transplant recipients, patients with ischemic injury and/or shock, and/or autoimmune diseases with a stem cell mobilizer in combination with an immunosuppressive agent. Generally, stem cell mobilizers include, but are not limited to, small organic molecules, polypeptides, nucleic acids, and carbohydrates.

In the case of a polypeptide, the stem cell mobilizer may comprise a cytokine, a colony stimulating factor, a protease or a chemokine. More specifically, the cytokine may include, but is not limited to, interleukin-1 (IL-1), interleukin-3 (IL-3), interleukin-6 (IL-6), interleukin-11 (IL-11), interleukin-7 (IL-7), and interleukin-12 (IL12).

In the case of a colony stimulating factor, the stem cell mobilizer may include, but is not limited to, granulocyte colony stimulating factor (G-CSF), granulocyte-macrophage colony stimulating factor (GM-CSF), macrophage colony stimulating factor (M-CSF), stem cell factor, FLT-3 ligand or a combination thereof.

In another embodiment, the protease stem cell mobilizer may include, but is not limited to, metalloproteinase (like MMP2 or MMP9) a serine protease, (like cathepsin G, or elastase) a cysteine protease (like cathepsin K) and a dipeptidyl peptidase-1 (DDP-1 OR CD26).

In yet another embodiment, the chemokine stem cell mobilizer may include, but is not limited to, CXCL12, IL-8, Mip-1α, and Groβ.

In yet another embodiment, the nucleic acid stem cell mobilizer is a DNA or an RNA molecule. In more specific embodiments, the nucleic acid can be a small interfering RNA (siRNA) molecule or an antisense molecule specific for CXCL12.

In the case of a carbohydrate, the stem cell mobilizer can be a sulfated carbohydrate may include, but is not limited to, Fucoidan and sulfated dextran. Fucoidan is a carbohydrate consisting of L-fucose, sulfate and acetate in a molar proportion of 1:1.23:0.36 and can be isolated from the Pacific brown seaweed Fucus evanescens. See Bilan et al., 337(8) CARBOHYDRATE RESEARCH 719-30 (2002). Sulfated dextrans refer to a series of polysaccharides that have variable sulfated patterns. See, e.g. Pomin et al., 15(12) GLYCOBIOLOGY 1376-1385 (2005); Melo et al., 279(2) J. BIOL. CHEM. 20824-20835 (2004); and Farias et al., 275(38) J. BIOL. CHEM. 29299-29307 (2000).

Stem cell mobilizers may further include, but are not limited to, AMD3100; stromal cell-derived factor (SDF-1); SDF-1 analogs (e.g., CTCE-0214 (Chemokine Therapeutics Corp.)); anti-SDF-1 antibodies; cyclophosphamide; stem cell factor (SCF); filgrastim; ancestim; Myeloid Progenitor Inhibitory Factor-1 (MPIF-1) (see U.S. Patent Publication No. 20080274109); and Very Late Antigen (VLA-4) antagonists (e.g., an alpha-4 integrin antagonist, such as an antibody including Natalizumab or Anti-phospho-Integrin α4 (Ser988), clone 6.33 (Upstate Cell Signaling Solutions), or a peptide (e.g., phenylacetyl-leu-asp-phe-D-prolineamide (Cytel Corp., San Diego Calif.))).

In particular embodiments, the stem cell mobilizer comprises a CXCR4 antagonist. In specific embodiments, the CXCR4 antagonist is TG-0054 (Burixafor; Phosphonic acid, p-(2-(4-(6-amino-2-(((trans-4-(((3-(cyclohexylamino)propyl)amino)methyl)cyclohexyl)methyl) amino)-4-pyrimidinyl)-1-piperazinyl)ethyl)-) (TaiGen Biotechnology Co., Ltd. (Taipei, Taiwan)). In other specific embodiments, the CXCR4 antagonist is AMD3465 (N-(pyridin-2-ylmethyl)-1-[4-(1,4,8,11-tetrazacyclotetradec-1-ylmethyl)phenyl] methanamine). In yet other embodiments, the CXCR4 antagonist is AMD3100. AMD3100 (1,1'-[1,4-phenylenebis (methylene)]bis-1,4,8,11-tetraazacyclo-tetradecane) is a symmetric bicyclam, prototype non-peptide antagonist of the CXCR4 chemokine receptor. See U.S. Pat. Nos. 6,835, 731 and 6,825,351. The term "AMD" or "AMD3100" is used interchangeably with Plerixafor, rINN, USAN, JM3100, and its trade name, Mozobil™. For convenience, the term "Plerixafor" is used throughout to refer to a CXCR4 antagonist.

The present invention also contemplates using mimetics of AMD3100. Mutational substitutions at 16 positions located in TM-III, -IV, -V, -VI, and -VII lining the main ligand-binding pocket of the CXCR4 receptor have identified three acid residues: Asp$^{171}$(AspIV:20), Asp$^{262}$ (AspVI: 23), and Glu$^{288}$ (GluVII:06) as the main interaction points for AMD3100. Molecular modeling suggests that one cyclam ring of AMD3100 interacts with Asp$^{171}$ in TM-IV, whereas the other ring is sandwiched between the carboxylic acid groups of Asp$^{262}$ and Glu$^{288}$ from TM-VI and -VII, respectively. In one study, it was found that introduction of only a Glu at position VII:06 and the removal of a neutralizing Lys residue at position VII:02 resulted in a 1000-fold increase in affinity of AMD3100 to within 10-fold of its affinity in CXCR4. Thus, mimetics, such as for example, peptide or non-peptide antagonists with improved oral bioavailability can be designed to efficiently and selectively block the CXCR4 receptor.

In other embodiments, the stem cell mobilizer is BKT140 (Biokin Therapeutics, Ltd. (Rehovot, Israel). BKT140 (4F-benzoyl-TN14003) binds and inhibits the CXCR4 chomokin receptor with high affinity, showing an IC$_{50}$ of ~1 nmol/L compared with the values obtained with AMD3100. Moreover, BKT140 hinders the cell migration stimulated by CXCL12 within IC$_{50}$ values of 0.5 to 2.5 nmol/L compared with IC$_{50}$ value of 51±17 nmol/L for Plerixafor, suggesting a high mobilization capacity. See Peled et al., 20 CLIN. CANCER RES. 469-79 (2013).

III. Immunosuppressive Agents

In conjunction with a stem cell mobilizer, immunosuppressive agents can be used to treat organ transplant recipients, patients with ischemic injury and/or shock, and/or autoimmune diseases. The term "immunosuppressive agent" refers to an agent that inhibits, slows or reverses the activity of the immune system. Immunosuppressive agents act by suppressing the function of responding immune cells (including, for example, T cells), directly (e.g., by acting on the immune cell) or indirectly (by acting on other mediating cells). Immunosuppressive agents can be given to a subject to prevent the subject's immune system from mounting an immune response after an organ transplant or for treating a disease that is caused by an overactive immune system.

A number of immunosuppressive agents that suppress the function of immunocompetent cells are used to suppress the immunological rejection (graft rejection) accompanying such transplantations, because the immunological rejection caused by allotransplantation is mainly due to cellular immunity. Such immunosuppressive agents include, but are not limited to, a calcineurin inhibitor (e.g., cyclosporin (CsA) and analogs thereof; ISA(TX) 247, and tacrolimus (FK-506)); azathioprine (AZ); mycophenolate mofetil (MMF); mizoribine (MZ); leflunomide (LEF); adrenocortical steroids (also known as adrenocortical hormones, corticosteroids, or corticoids) such as prednisolon and methyl-prednisolon; sirolimus (also known as rapamycin); everolimus; FK778; TAFA-93; deoxyspergualin (DSG); and FTY720 (chemical name: 2-amino-2-[2-(4-octylphenyl) ethyl]-1,3-propanediol hydrochloride).

In other embodiments, the immunosuppressive agent can include, but is not limited to, cyclophosphamide; 15-deoxyspergualin (Gusperimus); interferons; sulfasalazine; mimoribine, misoprostol, anti-IL-2 receptor antibodies, thalidomide, anti-tumor necrosis factor antibodies, anti-CD2 antibodies, anti-CD147 antibodies, anti-CD4 antibodies, anti-CD8 antibodies and anti-thymocyte globulin antibodies. Immunosuppressive agents also include ORTHOCLONE® (OKT3) (Ortho Biotech, Raritan, N.J.), SANDIMMUNE200 ORAL (cyclosporine) (Sandoz Pharmaceuticals, Hanover, N.J.), PROGRAF® (tacrolimus) (Fujisawa Pharmaceuticals, Deerfield, Ill.), CELLCEPT® (mycophenolate) (Roche Pharmaceuticals, Nutley, N.J.) and RAPAMUNE® (sirolimus) (Wyeth, Collegeville, Pa.). Optionally, the immunosuppressive agent is rapamycin, tacrolimus, mycophenolic acid, azathioprine or cyclophosphamide.

Immunosuppressive agents can further include an interleukin-2 α-chain blocker (e.g., basiliximab and daclizumab); an inhibitor of inosine monophosphate dehydrogenase (e.g., mycophenolate mofetil); and an inhibitor of dihydrofolic acid reductase (e.g., methotrexate).

In particular embodiments, the immunosuppressive agent is Tacrolimus. Tacrolimus (also FK-506 or Fujimycin) is an immunosuppressive drug that is mainly used after allogeneic organ transplant to reduce the activity of the patient's immune system and so lower the risk of organ rejection. It reduces interleukin-2 (IL-2) production by T-cells. It is also used in a topical preparation in the treatment of severe atopic dermatitis (eczema), severe refractory uveitis after bone marrow transplants, and the skin condition vitiligo. It is a 23-membered macrolide lactone discovered in 1984 from the fermentation broth of a Japanese soil sample that contained the bacteria *Streptomyces tsukubaensis*. The drug is sold under the trade names Prograf® given twice daily (intravenous), Advagraf® a sustained release formulation allowing once daily dosing (oral), and Protopic® the topical formulation. In particular embodiments, a low dose of Tacrolimus is used in combination with a stem cell mobilizer, e.g., plerixafor. Notably, in certain embodiments, a low dose of Tacrolimus can act as a stem cell mobilizer and an immunosuppressive agent.

IV. FK Binding Protein Ligands

In conjunction with at least one stem cell mobilizer, the pharmaceutical compositions and methods can also comprise a FK binding protein ligand. Examples include FK-506 and derivatives/analogs thereof including 506BD and L0685,818; rapamycin and derivatives/analogs thereof including Way-124466, RAD001, CCI-779, and AP23573; ascomycin and derivatives/analogs thereof including pimecrolimus. See Liu et al., 23(11) EXPERT OPIN. THER. PATENTS 1435-49 (2013). Furthermore, although the immunosuppressive agent tacrolimus/FK-506 is an FK binding protein ligand, in certain embodiments, an FK binding protein ligand can comprise a non-immuno suppressive FK binding protein ligand. Examples of non-immunosuppressive ligands include meridamycin, antascomicins, and synthetic ligand of FKBP (SLF).

V. Pharmaceutical Compositions and Administration

Accordingly, a pharmaceutical composition of the present invention may comprise an effective amount of a stem cell mobilizer and/or an immunosuppressive agent. The present invention further contemplates the use of an agent that has characteristics of both a stem cell mobilizer and an immunosuppressive agent. For example, Tacrolimus may be used as both a stem cell mobilizer and an immunosuppressive agent. Still further, the present invention contemplates the use of an effective amount of at least one stem cell mobilizer and/or at least one immunosuppressive agent. As used herein, the term "effective," means adequate to accomplish a desired, expected, or intended result. More particularly, an "effective amount" or a "therapeutically effective amount" is used interchangeably and refers to an amount of a stem cell mobilizer and/or an immunosuppressive agent, perhaps in further combination with yet another therapeutic agent, necessary to provide the desired "treatment" (defined herein) or therapeutic effect, e.g., an amount that is effective to prevent, alleviate, treat or ameliorate symptoms of a disease or prolong the survival of the subject being treated. In particular embodiments, the pharmaceutical compositions of the present invention are administered in a therapeutically effective amount to treat organ transplant recipients, patients with ischemic injury and/or shock, and/or autoimmune diseases. As would be appreciated by one of ordinary skill in the art, the exact amount required will vary from subject to subject, depending on age, general condition of the subject, the severity of the condition being treated, the particular compound and/or composition administered, and the like. An appropriate "therapeutically effective amount" in any individual case can be determined by one of ordinary skill in the art by reference to the pertinent texts and literature and/or by using routine experimentation.

In certain embodiments, the immunosuppressive agent (e.g., Tacrolimus) is administered in low dose amount. The phrase "low dose" or "low dose amount" of Tacrolimus in the context of the present invention (in combination with a stem cell mobilizer or alone) refers to the use of a particular amount of an immunosuppressive (e.g., Tacrolimus) that is lower than typically used for immunosuppression. In certain embodiments, the low dose is about 1/10 of the amount used for immunosuppression. In other embodiments, the low dose of Tacrolimus is about 1/2, about 1/3, about 1/4, about 1/5, about 1/6, about 1/7, about 1/8, or about 1/9 of the amount used for immunosuppression. In further embodiments, the low dose of Tacrolimus is about 0.9 times, about 0.8 times, about 0.7 times, about 0.6 times, about 0.5 times, about 0.4 times, about 0.3 times, about 0.2 times, about 0.1 times, about 0.09 times, about 0.08 times, about 0.07 times, about 0.06 times, about 0.05 times, about 0.04 times, about 0.03 times, about 0.02 times, about 0.01 times, about 0.009 times, about 0.08 times or about 0.07 times less than the typical amount used for a particular situation (i.e., typical immunosuppression amounts may differ). In specific embodiments, a low dose of an immunosuppressive agent (e.g., Tacrolimus) is about 0.01 mg/kg to about 0.5 mg/kg, more specifically, about 0.01 mg/kg to 0.5 mg/kg, about 0.01 mg/kg to about 0.45 mg/kg, about 0.01 mg/kg to about 0.4 mg/kg, about 0.01 mg/kg to about 0.35 mg/kg, about 0.06 mg/kg to about 0.45 mg/kg, about 0.07 mg/kg to about 0.4 mg/kg, about 0.08 mg/kg to about 0.35 mg/kg, about 0.09 mg/kg to about 0.3 mg/kg, about 0.1 mg/kg to about 0.25 mg/kg, and so on. In a specific embodiment, the low dose of Tacrolimus is about 0.01 mg/kg to 0.074 mg/kg.

A normal dose of Tacrolimus for immunosuppression is about 0.1 mg/kg/day-0.3 mg/kg/day (oral) and about 0.01 mg/kg/day-0.05 mg/kg/day (IV). In certain embodiments, a low dose of Tacrolimus is about one tenth the normal dose, e.g., about 0.01 mg/kg/day-0.03 mg/kg/day (oral) and about 0.001 mg/kg/day-0.005 mg/kg/day (IV). In other embodiments a low dose of Tacrolimus is about 1/5, 1/6, 1/7, 1/8, 1/9, 1/10, 1/11, 1/12, 1/13, 1/14, or at least 1/15 of a normal dose used for immunosuppression.

In other embodiments, a low dose of Tacrolimus comprises any amount below about 0.075 mg/kg/day for oral administration. The low dose can comprise any amount below about 0.07, 0.065, 0.06, 0.055, 0.05, 0.045, 0.04, 0.035, 0.03, 0.029, 0.028, 0.027, 0.026, 0.025, 0.024, 0.023, 0.022, 0.021, 0.020, 0.019, 0.018, 0.017, 0.016, 0.05, 0.014, 0.013, 0.012, 0.011, 0.010, 0.009, 0.008, 0.007, 0.006, 0.005, 0.004, 0.003, 0.002, or 0.001 mg/kg/day.

For intravenous administration, a low dose of Tacrolimus comprises any amount below about 0.01 mg/kg/day. The low dose can comprise any amount below about 0.01, 0.009, 0.008, 0.007, 0.006, 0.005, 0.004, 0.003, 0.002, or 0.001 mg/kg/day.

In further embodiments, a low dose of Tacrolimus results in a blood concentration range of about 0.1 ng/ml to about 10 ng/ml. The concentration can be less than about 10 ng/ml, 9 ng/ml, 8 ng/ml, 7 ng/ml, 6 ng/ml, 5 ng/ml, 4 ng/ml, 3 ng/ml, 2 ng/ml, 1 ng/ml, 0.9 ng/ml, 0.8 ng/ml, 0.7 ng/ml, 0.6 ng/ml, 0.5 ng/ml, 0.4 ng/ml, 0.3 ng/ml, 0.2 ng/ml, or 0.1 ng/ml. In a more specific embodiment, the blood tacrolimus concentrations are less than about 5 ng/ml for both oral and IV.

The pharmaceutical compositions of the present invention are in biologically compatible form suitable for administration in vivo for subjects. The pharmaceutical compositions can further comprise a pharmaceutically acceptable carrier. The term "pharmaceutically acceptable" means approved by a regulatory agency of the Federal or a state government or listed in the U.S. Pharmacopeia or other generally recognized pharmacopeia for use in animals, and more particularly, in humans. The term "carrier" refers to a diluent, adjuvant, excipient, or vehicle with which the stem cell mobilizer and/or the immunosuppressive agent are administered. Such pharmaceutical carriers can be sterile liquids, such as water and oils, including those of petroleum, animal, vegetable or synthetic origin, including but not limited to peanut oil, soybean oil, mineral oil, sesame oil and the like. Water may be a carrier when the pharmaceutical composition is administered orally. Saline and aqueous dextrose may be carriers when the pharmaceutical composition is administered intravenously. Saline solutions and aqueous dextrose and glycerol solutions may be employed as liquid carriers for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried slim milk, glycerol, propylene, glycol, water, ethanol and the like. The pharmaceutical composition may also contain minor amounts of wetting or emulsifying agents, or pH buffering agents.

The pharmaceutical compositions of the present invention can take the form of solutions, suspensions, emulsions, tablets, pills, capsules, powders, sustained-release formulations and the like. The composition can be formulated as a suppository, with traditional binders and carriers such as triglycerides. Oral formulation may include standard carriers such as pharmaceutical grades of mannitol, lactose, starch, magnesium stearate, sodium saccharine, cellulose, magnesium carbonate, etc. In a specific embodiment, a pharmaceutical composition comprises an effective amount of a stem cell mobilizer and/or an immunosuppressive agent together with a suitable amount of a pharmaceutically acceptable carrier so as to provide the form for proper administration to the patient. The formulation should suit the mode of administration.

The pharmaceutical compositions of the present invention may be administered by any particular route of administration including, but not limited to oral, parenteral, subcutaneous, intramuscular, intravenous, intrarticular, intrabronchial, intraabdominal, intracapsular, intracartilaginous, intracavitary, intracelial, intracelebellar, intracerebroventricular, intracolic, intracervical, intragastric, intrahepatic, intramyocardial, intraosteal, intraosseous, intrapelvic, intrapericardiac, intraperitoneal, intrapleural, intraprostatic, intrapulmonary, intrarectal, intrarenal, intraretinal, intraspinal, intrasynovial, intrathoracic, intrauterine, intravesical, bolus, vaginal, rectal, buccal, sublingual, intranasal, iontophoretic means, or transdermal means. Most suitable routes are oral administration or injection. In certain embodiments, subcutaneous injection is preferred.

In general, the pharmaceutical compositions comprising a stem cell mobilizer and/or an immunosuppressive agent disclosed herein may be used alone (e.g., a stem cell mobilizer administered with an immunosuppressive agent) or in concert with other therapeutic agents at appropriate dosages defined by routine testing in order to obtain optimal efficacy while minimizing any potential toxicity. The dosage regimen utilizing a pharmaceutical composition of the present invention may be selected in accordance with a variety of factors including type, species, age, weight, sex, medical condition of the patient; the severity of the condition to be treated; the route of administration; the renal and hepatic function of the patient; and the particular pharmaceutical composition employed. A physician of ordinary skill can readily determine and prescribe the effective amount of the pharmaceutical composition (and potentially other agents including therapeutic agents) required to prevent, counter, or arrest the progress of the condition.

Optimal precision in achieving concentrations of the therapeutic regimen (e.g., pharmaceutical compositions comprising a stem cell mobilizer and/or an immunosuppressive agent in combination with another therapeutic agent) within the range that yields maximum efficacy with minimal toxicity may require a regimen based on the kinetics of the pharmaceutical composition's availability to one or more target sites. Distribution, equilibrium, and elimination of a pharmaceutical composition may be considered when determining the optimal concentration for a treatment regimen. The dosages of a pharmaceutical composition disclosed herein may be adjusted when combined to achieve desired effects. On the other hand, dosages of the pharmaceutical compositions and various therapeutic agents may be independently optimized and combined to achieve a synergistic result wherein the pathology is reduced more than it would be if either was used alone.

In particular, toxicity and therapeutic efficacy of a pharmaceutical composition disclosed herein may be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effect is the therapeutic index and it may be expressed as the ratio $LD_{50}/ED_{50}$. Pharmaceutical compositions exhibiting large therapeutic indices are preferred except when cytotoxicity of the composition is the activity or therapeutic outcome that is desired. Although pharmaceutical compositions that exhibit toxic side effects may be used, a delivery system can target such compositions to the site of affected tissue in order to minimize potential damage to uninfected cells and, thereby, reduce side effects. Generally, the pharmaceutical compositions of the present invention may be administered in a manner that maximizes efficacy and minimizes toxicity.

Data obtained from cell culture assays and animal studies may be used in formulating a range of dosages for use in humans. The dosages of such compositions lie preferably within a range of circulating concentrations that include the $ED_{50}$ with little or no toxicity. The dosage may vary within this range depending upon the dosage form employed and the route of administration utilized. For any composition used in the methods of the invention, the therapeutically effective dose may be estimated initially from cell culture assays. A dose may be formulated in animal models to achieve a circulating plasma concentration range that includes the $IC_{50}$ (the concentration of the test composition that achieves a half-maximal inhibition of symptoms) as determined in cell culture. Such information may be used to accurately determine useful doses in humans. Levels in plasma may be measured, for example, by high performance liquid chromatography.

Moreover, the dosage administration of the compositions of the present invention may be optimized using a pharmacokinetic/pharmacodynamic modeling system. For example, one or more dosage regimens may be chosen and a pharmacokinetic/pharmacodynamic model may be used to determine the pharmacokinetic/pharmacodynamic profile of one or more dosage regimens. Next, one of the dosage regimens for administration may be selected which achieves the desired pharmacokinetic/pharmacodynamic response based on the particular pharmacokinetic/pharmacodynamic profile. See WO 00/67776, which is entirely expressly incorporated herein by reference.

In certain embodiments, the immunosuppressive agent is administered in low dose amount. The phrase "low dose" or "low dose amount" of an immunosuppressive agent in the context of the present invention (in combination with a stem cell mobilizer) refers to the use of a particular amount of an immunosuppressive drug that is lower than typically used for immunosuppression. In a specific embodiment, the low dose amount refers to the use of a particular amount that is lower than typically use for immunosuppression of an organ transplant recipient (i.e., an amount that prevents rejection).

The following description is made in the context of Tacrolimus, but the invention is not so limited. In certain embodiments a low dose of Tacrolimus is less than about 1/5, 1/6, 1/7, 1/8, 1/9, 1/10, 1/11, 1/12, 1/13, 1/14, or less then about 1/15 of a normal dose used for immunosuppression. In certain embodiments, the low dose of Tacrolimus is about or less than about 1/10 of the amount used for immunosuppression.

In other embodiments, the low dose of the immunosuppressive agent is about or less than 1/2, 1/3, 1/4, 1/5, 1/6, 1/7, 1/8, or about or less than about 1/9 of the amount used for immunosuppression. In further embodiments, the low dose of the immunosuppressive agent is about or less than about 0.9, 0.8, 0.7, 0.6, 0.5, 0.4, 0.3, 0.2, 0.1, 0.09, 0.08, 0.07, 0.06, 0.05, 0.04, 0.03, 0.02, 0.01, 0.009, 0.08, or 0.07 times than the typical amount used for a particular situation (i.e., typical immunosuppression amounts may differ).

In specific embodiments, a low dose of an immunosuppressive agent (e.g., Tacrolimus) is about 0.01 mg/kg to about 0.5 mg/kg, more specifically, about 0.01 mg/kg to 0.5 mg/kg, about 0.01 mg/kg to about 0.45 mg/kg, about 0.01 mg/kg to about 0.4 mg/kg, about 0.01 mg/kg to about 0.35 mg/kg, about 0.06 mg/kg to about 0.45 mg/kg, about 0.07 mg/kg to about 0.4 mg/kg, about 0.08 mg/kg to about 0.35 mg/kg, about 0.09 mg/kg to about 0.3 mg/kg, about 0.1 mg/kg to about 0.25 mg/kg, and so on. In a specific embodiment, the low dose of Tacrolimus is about 0.01 mg/kg to 0.074 mg/kg.

A normal dose of Tacrolimus for immunosuppression is about 0.1 mg/kg/day-0.3 mg/kg/day (oral) and about 0.01 mg/kg/day-0.05 mg/kg/day (IV). In certain embodiments, a low dose of Tacrolimus is about one tenth the normal dose, e.g., about 0.01 mg/kg/day-0.03 mg/kg/day (oral) and about 0.001 mg/kg/day-0.005 mg/kg/day (IV).

In other embodiments, a low dose of Tacrolimus comprises any amount below about 0.1 mg/kg/day for oral administration. The low dose can comprise any amount below about 0.095, 0.09, 0.085, 0.08, 0.075, 0.07, 0.065, 0.06, 0.055, 0.05, 0.045, 0.04, 0.035, 0.03, 0.029, 0.028, 0.027, 0.026, 0.025, 0.024, 0.023, 0.022, 0.021, 0.020, 0.019, 0.018, 0.017, 0.016, 0.05, 0.014, 0.013, 0.012, 0.011, 0.010, 0.009, 0.008, 0.007, 0.006, 0.005, 0.004, 0.003, 0.002, or 0.001 mg/kg/day.

For intravenous administration, a low dose of Tacrolimus comprises any amount below about 0.01 mg/kg/day. The low dose can comprise any amount below about 0.01, 0.009, 0.008, 0.007, 0.006, 0.005, 0.004, 0.003, 0.002, or 0.001 mg/kg/day.

In further embodiments, a low dose of Tacrolimus results in a blood concentration range of about 0.1 ng/ml to about 10 ng/ml. The concentration can be less than about 10 ng/ml, 9 ng/ml, 8 ng/ml, 7 ng/ml, 6 ng/ml, 5 ng/ml, 4 ng/ml, 3 ng/ml, 2 ng/ml, 1 ng/ml, 0.9 ng/ml, 0.8 ng/ml, 0.7 ng/ml, 0.6 ng/ml, 0.5 ng/ml, 0.4 ng/ml, 0.3 ng/ml, 0.2 ng/ml, or 0.1 ng/ml. In a more specific embodiment, the blood tacrolimus concentrations are less than about 5 ng/ml. In certain embodiments, the blood Tacrolimus concentrations are about 0.5-4 ng/ml. The concentration can range from about 0.1, 0.2, 0.3 0.4 or 0.5 ng/ml to about 1, 2, 3, 4, or 5 ng/ml.

In certain embodiments, the stem cell mobilizer is AMD3100. In such embodiments, the pharmaceutical composition can comprise a typical dose for AMD3100. This drug is typically administered to human patients at about 0.12-0.24 mg/kg. In a patient who has 60 kg body weight, the dosage of ADM3100 is about 0.24 mg/kg/day by subcutaneous injection.

The pharmaceutical compositions can be described in terms of a ratio of (a) an immunosuppressive drug or a FKBP ligand (including an immunosuppressive or a non-immunosuppressive FKBP ligand) to (b) a stem cell mobilizer (e.g., a CXCR antagonist). In certain embodiments, the ratio can be 1/1, 1/2, 1/3, 1/4, 1/5, 1/6, 1/7, 1/8, 1/9, 1/10, 1/11, 1/12, 1/13, 1/14, 1/15, 1/16, 1/17, 1/18, 1/19, 1/20, 1/21, 1/22, 1/23, 1/24, 1/25, 1/26, 1/27, 1/28, 1/29, 1/30, 1/31, 1/32, 1/33, 1/34, 1/35, 1/36, 1/37, 1/38, 1/39, 1/40, 1/41, 1/42, 1/43, 1/44, 1/45, 1/46, 1/47, 1/48, 1/49, 1/50, 1/51, 1/52, 1/53, 1/54, 1/55, 1/56, 1/57, 1/58, 1/59, 1/60, 1/61, 1/62, 1/63, 1/64, 1/65, 1/66, 1/67, 1/68, 1/69, 1/70, 1/71, 1/72, 1/73, 1/74, 1/75, 1/76, 1/77, 1/78, 1/79, 1/80, 1/81, 1/82, 1/83, 1/84, 1/85, 1/86, 1/87, 1/88, 1/89, 1/90, 1/91, 1/92, 1/93, 1/94, 1/95, 1/96, 1/97, 1/98, 1/99, 1/100, or more.

The pharmaceutical compositions can comprise (a) an immunosuppressive drug or a FKBP ligand (including an immunosuppressive or a non-immunosuppressive FKBP ligand) and (b) a stem cell mobilizer in a ratio range of about 1/10-1/100, 1/10-1/99, 1/10-1/98, 1/10-1/97, 1/10-1/96, 1/10-1/95, 1/10-1/94, 1/10-1/93, 1/10-1/92, 1/10-1/91, 1/10-1/90, 1/10-1/89, 1/10-1/88, 1/10-1/87, 1/10-/86, 1/10-1/85, 1/10-1/84, 1/10-1/83, 1/10-1/82, 1/10-1/81, 1/10-1/80, 1/10-1/79, 1/10-1/78, 1/10-1/77, 1/10-1/76, 1/10-1/75, 1/10-1/74, 1/10-1/73, 1/10-1/72, 1/10-1/71, 1/10-1/70, 1/10-1/69, 1/10-1/68, 1/10-1/67, 1/10-1/66, 1/10-1/65, 1/10-1/64, 1/10-1/63, 1/10-1/62, 1/10-1/61, 1/10-1/60, 1/10-1/59, 1/10-1/58, 1/10-1/57, 1/10-1/56, 1/10-1/55, 1/10-1/54, 1/10-1/53, 1/10-1/52, 1/10-1/51, 1/10-1/50, 1/10-1/49, 1/10-1/48, 1/10-1/47, 1/10-1/46, 1/10-1/45, 1/10-1/44, 1/10-1/43, 1/10-1/42, 1/10-1/41, 1/10-1/40, 1/10-1/39, 1/10-1/38, 1/10-1/37, 1/10-1/36, 1/10-1/35, 1/10-1/34, 1/10-1/33, 1/10-1/32, 1/10-1/31, 1/10-1/30, 1/10-1/29, 1/10-1/28, 1/10-1/27, 1/10-1/26, 1/10-1/25, 1/10-1/24, 1/10-1/23, 1/10-1/22, 1/10-1/21, 1/10-1/20, 1/10-1/19, 1/10-1/18, 1/10-1/17, 1/10-1/16, 1/10-1/15, 1/10-1/14, 1/10-1/13, 1/10-1/12, or 1/10-1/11.

In alternative embodiments, the pharmaceutical compositions can comprise (a) an immunosuppressive drug or a FKBP ligand (including an immunosuppressive or a non-immunosuppressive FKBP ligand) and (b) a stem cell mobilizer in a ratio range of about 1/15-1/100, 1/15-1/99, 1/15-1/98, 1/15-1/97, 1/15-1/96, 1/15-1/95, 1/15-1/94, 1/15-1/93, 1/15-1/92, 1/15-1/91, 1/15-1/90, 1/15-1/89, 1/15-1/88, 1/15-1/87, 1/15-1/86, 1/15-1/85, 1/15-1/84, 1/15-1/83, 1/15-1/82, 1/15-1/81, 1/15-1/80, 1/15-1/79, 1/15-1/78, 1/15-1/77, 1/15-1/76, 1/15-1/75, 1/15-1/74, 1/15-1/73, 1/15-1/72, 1/15-1/71, 1/15-1/70, 1/15-1/69, 1/15-1/68, 1/15-1/67, 1/15-1/66, 1/15-1/65, 1/15-1/64, 1/15-1/63, 1/15-1/62, 1/15-1/61, 1/15-1/60, 1/15-1/59, 1/15-1/58, 1/15-1/57, 1/15-1/56, 1/15-1/55, 1/15-1/54, 1/15-1/53, 1/15-1/52, 1/15-1/51, 1/15-1/50, 1/15-1/49, 1/15-1/48, 1/15-1/47, 1/15-1/46, 1/15-1/45, 1/15-1/44, 1/15-1/43, 1/15-1/42, 1/15-1/41, 1/15-1/40, 1/15-1/39, 1/15-1/38, 1/15-1/37, 1/15-1/36, 1/15-1/35, 1/15-1/34, 1/15-1/33, 1/15-1/32, 1/15-1/31, 1/15-1/30, 1/15-1/29, 1/15-1/28, 1/15-1/27, 1/15-1/26, 1/15-1/25, 1/15-1/24, 1/15-1/23, 1/15-1/22, 1/15-1/21, 1/15-1/20, 1/15-1/19, 1/15-1/18, 1/15-1/17, or 1/15-1/16.

The ratio range of (a) an immunosuppressive drug or a FKBP ligand (including an immunosuppressive or a non-immunosuppressive FKBP ligand) to (b) a stem cell mobilizer within a pharmaceutical composition can comprise about 1/20-1/100, 1/20-1/99, 1/20-1/98, 1/20-1/97, 1/20-1/96, 1/20-1/95, 1/20-1/94, 1/20-1/93, 1/20-1/92, 1/20-1/91, 1/20-1/90, 1/20-1/89, 1/20-1/88, 1/20-1/87, 1/20-1/86, 1/20-1/85, 1/20-1/84, 1/20-1/83, 1/20-1/82, 1/20-1/81, 1/20-1/80, 1/20-1/79, 1/20-1/78, 1/20-1/77, 1/20-1/76, 1/20-1/75, 1/20-1/74, 1/20-1/73, 1/20-1/72, 1/20-1/71, 1/20-1/70, 1/20-1/69, 1/20-1/68, 1/20-1/67, 1/20-1/66, 1/20-1/65, 1/20-1/64, 1/20-1/63, 1/20-1/62, 1/20-1/61, 1/20-1/60, 1/20-1/59, 1/20-1/58, 1/20-1/57, 1/20-1/56, 1/20-1/55, 1/20-1/54, 1/20-1/53, 1/20-1/52, 1/20-1/51, 1/20-1/50, 1/20-1/49, 1/20-1/48, 1/20-1/47, 1/20-1/46, 1/20-1/45, 1/20-1/44, 1/20-1/43, 1/20-1/42, 1/20-1/41, 1/20-1/40, 1/20-1/39, 1/20-1/38, 1/20-1/37, 1/20-1/36, 1/20-1/35, 1/20-1/34, 1/20-1/33, 1/20-1/32, 1/20-1/31, 1/20-1/30, 1/20-1/29, 1/20-1/28, 1/20-1/27, 1/20-1/26, 1/20-1/25, 1/20-1/24, 1/20-1/23, 1/20-1/22, or 1/20-1/21.

In other embodiments, the ratio range of (a) an immunosuppressive drug or a FKBP ligand (including an immunosuppressive or a non-immunosuppressive FKBP ligand) to (b) a stem cell mobilizer within a pharmaceutical composition can comprise about 1/30-1/100, 1/30-1/99, 1/30-1/98, 1/30-1/97, 1/30-1/96, 1/30-1/95, 1/30-1/94, 1/30-1/93, 1/30-1/92, 1/30-1/91, 1/30-1/90, 1/30-1/89, 1/30-1/88, 1/30-1/87, 1/30-1/86, 1/30-1/85, 1/30-1/84, 1/30-1/83, 1/30-1/82, 1/30-1/81, 1/30-1/80, 1/30-1/79, 1/30-1/78, 1/30-1/77, 1/30-1/76, 1/30-1/75, 1/30-1/74, 1/30-1/73, 1/30-1/72, 1/30-1/71, 1/30-1/70, 1/30-1/69, 1/30-1/68, 1/30-1/67, 1/30-1/66, 1/30-1/65, 1/30-1/64, 1/30-1/63, 1/30-1/62, 1/30-1/61, 1/301/60, 1/30-1/59, 1/30-1/58, 1/30-1/57, 1/30-1/56, 1/30-1/55, 1/30-1/54, 1/30-1/53, 1/30-1/52, 1/30-1/51, 1/30-1/50, 1/30-1/49, 1/30-1/48, 1/30-1/47, 1/30-1/46, 1/301/45, 1/30-1/44, 1/30-1/43, 1/30-1/42, 1/30-1/41, 1/30-1/40, 1/30-1/39, 1/30-1/38, 1/30-1/37, 1/30-1/36, 1/30-1/35, 1/30-1/34, 1/30-1/33, 1/30-1/32, or 1/30-1/31.

In further embodiments, the pharmaceutical compositions can comprise (a) an immunosuppressive drug or a FKBP ligand (including an immunosuppressive or a non-immunosuppressive FKBP ligand) and (b) a stem cell mobilizer in a ratio range of about 1/40-1/100, 1/40-1/99, 1/40-1/98, 1/40-1/97, 1/40-1/96, 1/40-1/95, 1/40-1/94, 1/40-1/93, 1/40-1/92, 1/40-1/91, 1/40-1/90, 1/40-1/89, 1/40-1/88, 1/40-1/87, 1/40-1/86, 1/40-1/85, 1/40-1/84, 1/40-1/83, 1/40-1/82, 1/40-1/81, 1/40-1/80, 1/40-1/79, 1/40-1/78, 1/40-1/77, 1/40-1/76, 1/40-1/75, 1/40-1/74, 1/40-1/73, 1/40-1/72, 1/40-1/71, 1/40-1/70, 1/40-1/69, 1/40-1/68, 1/40-1/67, 1/40-1/66, 1/40-1/65, 1/40-1/64, 1/40-1/63, 1/40-1/62, 1/40-1/61, 1/40-1/60, 1/40-1/59, 1/40-1/58, 1/40-1/57, 1/40-1/56, 1/40-1/55, 1/40-1/54, 1/40-1/53, 1/40-1/52, 1/40-1/51, 1/40-1/50, 1/40-1/49, 1/40-1/48, 1/40-1/47, 1/40-1/46, 1/40-1/45, 1/40-1/44, 1/40-1/43, 1/40-1/42, or 1/40-1/41.

In alternative embodiments, the pharmaceutical compositions can comprise (a) an immunosuppressive drug or a FKBP ligand (including an immunosuppressive or a non-immunosuppressive FKBP ligand) and a stem cell mobilizer in a ratio range of about 1/50-1/100, 1/50-1/99, 1/50-1/98, 1/50-1/97, 1/50-1/96, 1/50-1/95, 1/50-1/94, 1/50-1/93, 1/50-1/92, 1/50-1/91, 1/50-1/90, 1/50-1/89, 1/50-1/88, 1/50-1/87, 1/50-1/86, 1/50-1/85, 1/50-1/84, 1/50-1/83, 1/50-1/82, 1/50-1/81, 1/50-1/80, 1/50-1/79, 1/50-1/78, 1/50-1/77, 1/50-1/76, 1/50-1/75, 1/50-1/74, 1/50-1/73, 1/50-1/72, 1/50-1/71, 1/50-1/70, 1/50-1/69, 1/50-1/68, 1/50-1/67, 1/50-1/66, 1/50-1/65, 1/50-1/64, 1/50-1/63, 1/50-1/62, 1/50-1/61, 1/50-1/60, 1/50-1/59, 1/50-1/58, 1/50-1/57, 1/50-1/56, 1/50-1/55, 1/50-1/54, 1/50-1/53, 1/50-1/52, 1/50-1/51, 1/60-1/100, 1/60-1/99, 1/60-1/98, 1/60-1/97, 1/60-1/96, 1/60-1/95, 1/60-1/94, 1/60-1/93, 1/60-1/92, 1/60-1/91, 1/60-1/90, 1/60-1/89, 1/60-1/88, 1/60-1/87, 1/60-1/86, 1/60-1/85, 1/60-1/84, 1/60-1/83, 1/60-1/82, 1/60-1/81, 1/60-1/80, 1/60-1/79, 1/60-1/78, 1/60-1/77, 1/60-1/76, 1/60-1/75, 1/60-1/74, 1/60-1/73, 1/60-1/72, 1/60-1/71, 1/60-1/70, 1/60-1/69, 1/60-1/68, 1/60-1/67, 1/60-1/66, 1/60-1/65, 1/60-1/64, 1/60-1/63, 1/60-1/62, 1/60-1/61, In other embodiments, the ratio range of (a) an immunosuppressive drug or a FKBP ligand (including an immunosuppressive or a non-immunosuppressive FKBP ligand) to (b) a stem cell mobilizer within a pharmaceutical composition can comprise about 1/70-1/100, 1/70-1/99, 1/70-1/98, 1/70-1/97, 1/70-1/96, 1/70-1/95, 1/70-1/94, 1/70-1/93, 1/70-1/92, 1/70-1/91, 1/701/90, 1/70-1/89, 1/70-1/88, 1/70-1/87, 1/70-1/86, 1/70-1/85, 1/70-1/84, 1/70-1/83, 1/70-1/82, 1/70-1/81, 1/70-1/80, 1/70-1/79, 1/70-1/78, 1/70-1/77, 1/70-1/76, 1/70-1/75, 1/70-1/74, 1/70-1/73, 1/70-1/72, 1/70-1/71, 1/80-1/100, 1/80-1/99, 1/80-1/98, 1/80-1/97, 1/80-1/96, 1/80-1/95, 1/80-1/94, 1/80-1/93, 1/80-1/92, 1/80-1/91, 1/80-1/90, 1/80-1/89, 1/80-1/88, 1/80-1/87, 1/80-1/86, 1/80-1/85, 1/80-1/84, 1/80-1/83, 1/80-1/82, 1/80-1/81, 1/90-1/100, 1/90-1/99, 1/90-1/98, 1/90-1/97, 1/90-1/96, 1/90-1/95, 1/90-1/94, 1/90-1/93, 1/90-1/92, or 1/90-1/91.

In particular embodiments, the pharmaceutical compositions comprise (a) a non-immunosuppressive FKBP ligand and (b) a stem cell mobilizer (e.g., a CXCR antagonist). In such embodiments, the ratio of non-immunosuppressive FKBP ligand to stem cell mobilizer can be between 1/10 to 1/100, as recited herein. In further embodiments, the ratio can be greater than 1/10 including 1/1, 1/2, 1/3, 1/4, 1/5, 1/6, 1/7, 1/8 or 1/9. In other embodiments, the ratio can be less than 1/100 including, but not limited to, 1/150, 1/200, 1/250, 1/300, 1/350, 1/400, 1/450, and 1/500 or more (including ranges of the foregoing).

More specifically, the pharmaceutical compositions may be administered in a single daily dose, or the total daily dosage may be administered in divided doses of two, three, or four times daily. In the case of oral administration, the daily dosage of the compositions may be varied over a wide range from about 0.1 ng to about 1,000 mg per patient, per day. The range may more particularly be from about 0.001 ng/kg to 10 mg/kg of body weight per day, about 0.1-100 µg, about 1.0-50 µg or about 1.0-20 mg per day for adults (at about 60 kg).

The daily dosage of the pharmaceutical compositions may be varied over a wide range from about 0.1 ng to about 1000 mg per adult human per day. For oral administration, the compositions may be provided in the form of tablets containing from about 0.1 ng to about 1000 mg of the composition or 0.1, 0.2, 0.5, 1.0, 2.0, 5.0, 10.0, 15.0, 100, 150, 200, 250, 300, 350, 400, 450, 500, 550, 600, 650, 700, 800, 900, or 1000 milligrams of the composition for the symptomatic adjustment of the dosage to the patient to be treated. An effective amount of the pharmaceutical composition is ordinarily supplied at a dosage level of from about 0.1 ng/kg to about 20 mg/kg of body weight per day. In one embodiment, the range is from about 0.2 ng/kg to about 10 mg/kg of body weight per day. In another embodiment, the range is from about 0.5 ng/kg to about 10 mg/kg of body weight per day. The pharmaceutical compositions may be administered on a regimen of about 1 to about 10 times per day.

In the case of injections, it is usually convenient to give by an intravenous route in an amount of about 0.0001 µg-30 mg, about 0.01 µg-20 mg or about 0.01-10 mg per day to adults (at about 60 kg). In the case of other animals, the dose calculated for 60 kg may be administered as well. More specifically, in the case of injections, it is usually convenient to give Tacrolimus by a subcutaneous route in an amount of about 0.01 mg/kg to about 0.5 mg/kg of Tacrolimus, more specifically, about 0.01 mg/kg to 0.5 mg/kg, about 0.02 mg/kg to about 0.5 mg/kg, about 0.03 mg/kg to about 0.5 mg/kg, about 0.04 mg/kg to about 0.45 mg/kg, about 0.06 mg/kg to about 0.45 mg/kg, about 0.07 mg/kg to about 0.4 mg/kg, about 0.08 mg/kg to about 0.35 mg/kg, about 0.09 mg/kg to about 0.3 mg/kg, about 0.1 mg/kg to about 0.25 mg/kg, and so on.

Doses of a pharmaceutical composition of the present invention can optionally include 0.0001 µg to 1,000 mg/kg/administration, or 0.001 µg to 100.0 mg/kg/administration, from 0.01 µg to 10 mg/kg/administration, from 0.1 µg to 10 mg/kg/administration, including, but not limited to, 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 and/or 100-500 mg/kg/administration or any range, value or fraction thereof, or to achieve a serum concentration of 0.1, 0.5, 0.9, 1.0, 1.1, 1.2, 1.5, 1.9, 2.0, 2.5, 2.9, 3.0, 3.5, 3.9, 4.0, 4.5, 4.9, 5.0, 5.5, 5.9, 6.0, 6.5, 6.9, 7.0, 7.5, 7.9, 8.0, 8.5, 8.9, 9.0, 9.5, 9.9, 10, 10.5, 10.9, 11, 11.5, 11.9, 20, 12.5, 12.9, 13.0, 13.5, 13.9, 14.0, 14.5, 4.9, 5.0, 5.5, 5.9, 6.0, 6.5, 6.9, 7.0, 7.5, 7.9, 8.0, 8.5, 8.9, 9.0, 9.5, 9.9, 10, 10.5, 10.9, 11, 11.5, 11.9, 12, 12.5, 12.9, 13.0, 13.5, 13.9, 14, 14.5, 15, 15.5, 15.9, 16, 16.5, 16.9, 17, 17.5, 17.9, 18, 18.5, 18.9, 19, 19.5, 19.9, 20, 20.5, 20.9, 21, 22, 23, 24, 25, 26, 27, 28, 29, 30, 35, 40, 45, 50, 55, 60, 65, 70, 75, 80, 85, 90, 96, 100, 200, 300, 400, 500, 600, 700, 800, 900, 1000, 1500, 2000, 2500, 3000, 3500, 4000, 4500, and/or 5000 µg/ml serum concentration per single or multiple administration or any range, value or fraction thereof.

As a non-limiting example, treatment of subjects can be provided as a one-time or periodic dosage of a composition of the present invention 0.1 ng to 100 mg/kg such as 0.0001, 0.001, 0.01, 0.1 0.5, 0.9, 1.0, 1.1, 1.5, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 45, 50, 60, 70, 80, 90 or 100 mg/kg, per day, on at least one of day 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40, or alternatively or additionally, at least one of week 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, or 52, or alternatively or additionally, at least one of 1, 2, 3, 4, 5, 6, 7, 8, 9, 10, 11, 12, 13, 14, 15, 16, 17, 18, 19, or 20 years, or any combination thereof, using single, infusion or repeated doses.

In certain embodiments, doses of a pharmaceutical composition of the present invention can optionally include about 0.01 mg/kg to about 0.5 mg/kg of Tacrolimus including, but not limited to, 0.01, 0.02, 0.03, 0.04, 0.05, 0.06, 0.07, 0.08, 0.09, 0.1, 0.2, 0.3, 0.4, and/or 0.5 mg/kg/administration or any range, value or fraction thereof, or to achieve a blood level of about 2.0, 2.5, 2.9, 3.0, 3.5, 3.9, 4.0, 4.5, 4.9, 5.0, 5.5, 5.9, 6.0, 6.5, 6.9, 7.0, 7.5, 7.9, 8.0, 8.5, 8.9, 9.0, 9.5, 9.9, 10, 10.5, 10.9, 11, 11.5, 11.9, 20, 12.5, 12.9, 13.0, 13.5, 13.9, 14.0, 14.5, 4.9, 5.0, 5.5, 5.9, 6.0, 6.5, 6.9, 7.0, 7.5, 7.9, 8.0, 8.5, 8.9, 9.0, 9.5, 9.9, 10, 10.5, 10.9, 11, 11.5, 11.9, 12, 12.5, 12.9, 13.0, 13.5, 13.9, 14, 14.5, 15, 15.5, 15.9, 16, 16.5, 16.9, 17, 17.5, 17.9, 18, 18.5, 18.9, 19, 19.5, 19.9, 20 ng/ml.

Specifically, the pharmaceutical compositions of the present invention may be administered at least once a week over the course of several weeks. In one embodiment, the pharmaceutical compositions are administered at least once a week over several weeks to several months. In another embodiment, the pharmaceutical compositions are administered once a week over four to eight weeks. In yet another embodiment, the pharmaceutical compositions are administered once a week over four weeks.

More specifically, the pharmaceutical compositions may be administered at least once a day for about 2 days, at least once a day for about 3 days, at least once a day for about 4 days, at least once a day for about 5 days, at least once a day for about 6 days, at least once a day for about 7 days, at least once a day for about 8 days, at least once a day for about 9 days, at least once a day for about 10 days, at least once a day for about 11 days, at least once a day for about 12 days, at least once a day for about 13 days, at least once a day for about 14 days, at least once a day for about 15 days, at least once a day for about 16 days, at least once a day for about 17 days, at least once a day for about 18 days, at least once a day for about 19 days, at least once a day for about 20 days, at least once a day for about 21 days, at least once a day for about 22 days, at least once a day for about 23 days, at least once a day for about 24 days, at least once a day for about 25 days, at least once a day for about 26 days, at least once a day for about 27 days, at least once a day for about 28 days, at least once a day for about 29 days, at least once a day for about 30 days, or at least once a day for about 31 days.

Alternatively, the pharmaceutical compositions may be administered about once every day, about once every 2 days, about once every 3 days, about once every 4 days, about once every 5 days, about once every 6 days, about once every 7 days, about once every 8 days, about once every 9 days, about once every 10 days, about once every 11 days, about once every 12 days, about once every 13 days, about once every 14 days, about once every 15 days, about once every 16 days, about once every 17 days, about once every 18 days, about once every 19 days, about once every 20 days, about once every 21 days, about once every 22 days, about once every 23 days, about once every 24 days, about once every 25 days, about once every 26 days, about once every 27 days, about once every 28 days, about once every 29 days, about once every 30 days, or about once every 31 days.

The pharmaceutical compositions of the present invention may alternatively be administered about once every week, about once every 2 weeks, about once every 3 weeks, about once every 4 weeks, about once every 5 weeks, about once every 6 weeks, about once every 7 weeks, about once every 8 weeks, about once every 9 weeks, about once every 10 weeks, about once every 11 weeks, about once every 12 weeks, about once every 13 weeks, about once every 14 weeks, about once every 15 weeks, about once every 16 weeks, about once every 17 weeks, about once every 18 weeks, about once every 19 weeks, about once every 20 weeks.

Alternatively, the pharmaceutical compositions of the present invention may be administered about once every month, about once every 2 months, about once every 3 months, about once every 4 months, about once every 5 months, about once every 6 months, about once every 7 months, about once every 8 months, about once every 9 months, about once every 10 months, about once every 11 months, or about once every 12 months.

Alternatively, the pharmaceutical compositions may be administered at least once a week for about 2 weeks, at least once a week for about 3 weeks, at least once a week for about 4 weeks, at least once a week for about 5 weeks, at least once a week for about 6 weeks, at least once a week for about 7 weeks, at least once a week for about 8 weeks, at least once a week for about 9 weeks, at least once a week for about 10 weeks, at least once a week for about 11 weeks, at least once a week for about 12 weeks, at least once a week for about 13 weeks, at least once a week for about 14 weeks, at least once a week for about 15 weeks, at least once a week for about 16 weeks, at least once a week for about 17 weeks, at least once a week for about 18 weeks, at least once a week for about 19 weeks, or at least once a week for about 20 weeks.

Alternatively the pharmaceutical compositions may be administered at least once a week for about 1 month, at least once a week for about 2 months, at least once a week for about 3 months, at least once a week for about 4 months, at least once a week for about 5 months, at least once a week for about 6 months, at least once a week for about 7 months, at least once a week for about 8 months, at least once a week for about 9 months, at least once a week for about 10 months, at least once a week for about 11 months, or at least once a week for about 12 months.

The pharmaceutical compositions of the present invention (e.g., a stem cell mobilizer and/or an immunosuppressive agent) can be administered simultaneously or sequentially by the same or different routes of administration. The pharmaceutical compositions may further be combined with one or more additional therapeutic agents. The determination of the identity and amount of the pharmaceutical compositions for use in the methods of the present invention can be readily made by ordinarily skilled medical practitioners using standard techniques known in the art. In specific embodiments, a stem cell mobilizer of the present invention can be administered in combination with an effective amount of an immunosuppressive agent. In other specific embodiments, a stem cell mobilizer and an immunosuppressive agent can be administered in combination with an effective amount of another stem cell mobilizer, another immunosuppressive agent, or another therapeutic agent.

In various embodiments, the stem cell mobilizer of the present invention in combination with an immunosuppressive agent (and optionally another stem cell mobilizer, another immunosuppressive agent, or another therapeutic agent) may be administered at about the same time, less than 1 minute apart, less than 2 minutes apart, less than 5 minutes apart, less than 30 minutes apart, 1 hour apart, at about 1 hour apart, at about 1 to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, at about 12 hours to 18 hours apart, 18 hours to 24 hours apart, 24 hours to 36 hours apart, 36 hours to 48 hours apart, 48 hours to 52 hours apart, 52 hours to 60 hours apart, 60 hours to 72 hours apart, 72 hours to 84 hours apart, 84 hours to 96 hours apart, or 96 hours to 120 hours part. In particular embodiments, two or more therapies are administered within the same patent visit.

In certain embodiments, the stem cell mobilizer of the present invention in combination with an immunosuppressive agent (and optionally another stem cell mobilizer, another immunosuppressive agent, or another therapeutic agent) are cyclically administered. Cycling therapy involves the administration of a first therapy (e.g., the stem cell mobilizer) for a period of time, followed by the administration of a second therapy (e.g., the immunosuppressive agent) for a period of time, optionally, followed by the administration of perhaps a third therapy for a period of time and so forth, and repeating this sequential administration, e.g., the cycle, in order to reduce the development of resistance to one of the therapies, to avoid or reduce the side effects of one of the therapies, and/or to improve the efficacy of the therapies. In certain embodiments, the administration of the combination therapy of the present invention may be repeated and the administrations may be separated by at least 1 day, 2 days, 3 days, 5 days, 10 days, 15 days, 30 days, 45 days, 2 months, 75 days, 3 months, or at least 6 months.

Thus, in one aspect, a stem cell mobilizer is administered in combination with an immunosuppressive agent. In particular embodiments, the stem cell mobilizer (e.g., AMD3100) and immunosuppressive agent (e.g., Tacrolimus) is administered separately over a period of time following transplantation and/or injury. For example, the treatment regimen for a liver transplant recipient may comprise the following: AMD3465 (1 mg/kg) and Tacrolimus (0.1 mg/kg) at Day 0, 1, 2, 3 and 7 (subcutaneous injection). The treatment regimen may alternatively comprise the following: AMD (1 mg/kg) and Tacrolimus (0.1 mg/kg) at Day 0, 1, 2, 3, 7, 10 and 15 (subcutaneous injection).

As a non-limiting example in kidney transplantation, the treatment regimen may comprise AMD3100 (1 mg/kg) after reperfusion and Day 2, 4, 6, and 10 following transplantation, and Tacrolimus (0.05 mg/kg) after reperfusion and Day 1, 2, 3, 4, 5, 6, 7, and 10 following transplantation (subcutaneous injection). In embodiments involving skin transplantation, the treatment regimen may comprise the following: AMD3100 (1 mg/kg) immediately after transplantation and every two days thereafter, and Tacrolimus (0.1 mg/kg) every day following transplantation (subcutaneous injection).

Without further elaboration, it is believed that one skilled in the art, using the preceding description, can utilize the present invention to the fullest extent. The following examples are illustrative only, and not limiting of the remainder of the disclosure in any way whatsoever.

EXAMPLES

The following examples are put forth so as to provide those of ordinary skill in the art with a complete disclosure and description of how the compounds, compositions, articles, devices, and/or methods described and claimed herein are made and evaluated, and are intended to be purely illustrative and are not intended to limit the scope of what the inventors regard as their invention. Efforts have been made to ensure accuracy with respect to numbers (e.g., amounts, temperature, etc.) but some errors and deviations should be accounted for herein. Unless indicated otherwise, parts are parts by weight, temperature is in degrees Celsius or is at ambient temperature, and pressure is at or near atmospheric. There are numerous variations and combinations of reaction conditions, e.g., component concentrations, desired solvents, solvent mixtures, temperatures, pressures and other reaction ranges and conditions that can be used to optimize the product purity and yield obtained from the described process. Only reasonable and routine experimentation will be required to optimize such process conditions.

Example 1

Induction of Liver Allograft Acceptance by Mobilizing Bone Marrow Stem Cells

Materials and Methods

Rat Strains and Care. DA (RT1A$^a$) rats were purchased from Harlan ague-Dawley (Indianapolis, Ind.) and used at 8-12 weeks of age. The green fluorescent protein (GFP) transgenic Lewis (RT1$^1$) rat strain was obtained from the National Institutes of Health (NIH)-funded Rat Resource and Research Center (RRRC), University of Missouri, Columbia, Mo. Animals were maintained in the specific pathogen-free facility of Johns Hopkins Medical Institutions. Animals were cared for according to NIH guidelines and under a protocol approved by the Johns Hopkins University Animal Care Committee.

Liver Transplantation. Orthotopic liver transplantation (OLT) was performed under isoflurane (Abbott laboratories, North Chicago, Ill.) inhalation anesthesia according to a method modified from previously described. Small liver transplantation consisted of removal of the left lateral lobe, the left portion of the median lobe, and the anterior and posterior caudate lobes. This reduced the liver mass by about 50%. The livers were flushed in situ with 10 ml cold saline via the portal vein, explanted and immersed in cold saline solution. The host liver was excised by ligation and division of the right adrenal and lumbar veins. The hepatic artery was ligated and divided. The bile duct was cannulated by insertion of a tube 2 mm in length (outer diameter, 1.2 mm) via choledocotomy and secured with a circumferential 8-0 silk suture. The inferior vena cava and the portal vein were cross-clamped with microvessel clips. The suprahepatic vena cava was pulled down using a cotton tape passed around the host liver and cross-clamped with a baby Statinksy clamp. The vessels were divided and liver was removed. The donor suprahepatic vena cava was anstomosed end-to-end with the host suprahepatic vena cava with running 8-0 prolene. The portal vein and infra hepatic vena cava were anastomosed using the cuff technique described previously. The common bile duct of the donor was cannulated with the small tube residing in the host bile duct and tied in place. The hepatic artery was not reconstructed.

Experimental Groups and Animal Treatment. Transplanted rats were divided by four groups: (1) control group (treated with same volume of saline); (2) low dose of immunosuppressant (FK-506, 0.1 mg/kg/day); (3) stem cell mobilizer (AMD3100, 1 mg/kg/day); and (4) combination of low dose FK-506 and AMD3100. AMD3100 and/or FK-506 were injected subcutaneously immediately after reperfusion and day 1, 2, 3 and 7 following liver transplantation (FIG. 1). Some of the animals were sacrificed at day 3, 7 and 10 after transplantation and liver tissue, spleen and peripheral blood were collected.

Flow Cytometry. Single-cell suspensions ($5 \times 10^5$) of peripheral blood monocytes were analyzed for CD34, CXCR4, c-Kit, Thy-1, and Sca-1 expression. Nonspecific antibody binding was blocked with goat and rat serum (Sigma) for 30 minutes.

Histological Studies. Histological changes in liver tissue sections were evaluated by H&E staining. Recipient-derived GFP positive cells in liver tissue sections were analyzed by confocal fluorescence microscopy.

RT-PCR Analysis. The mRNA expression of CD34, CDCR4, SDF-1, SCF, c-Kit, c-Met and Foxp3 in livers and spleens was analyzed by using RT-PCR.

Results

Figure 2:
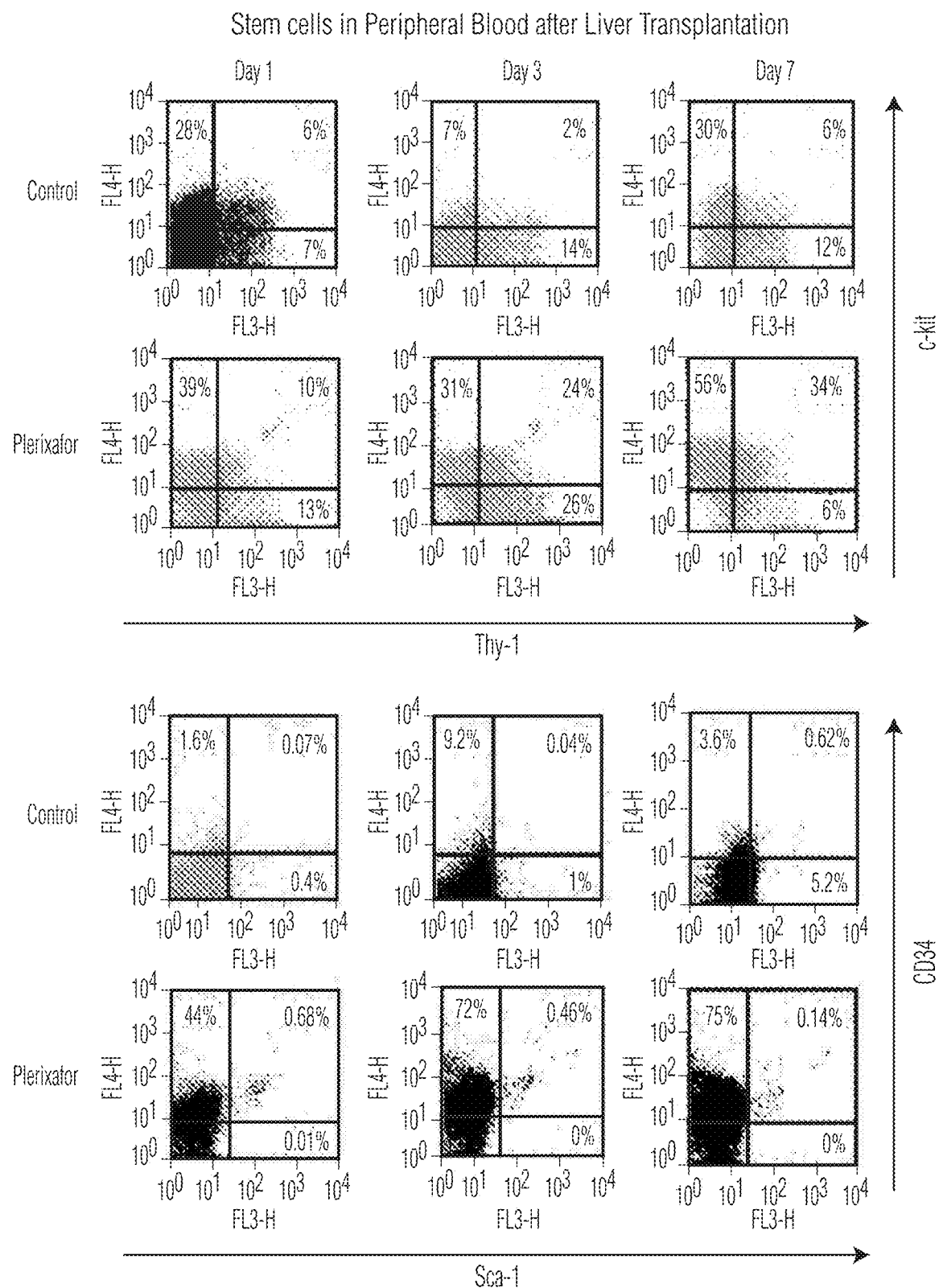
FIG. 2 shows the percentage of $CD34^+$, $c\text{-}Kit^+$, $Thy\text{-}1^-$ and $Sca1^+$ cells in peripheral blood in AMD treated animals compared to control animals after liver transplantation.

AMD Treatment Significantly Increases Stem Cell Populations in Peripheral Blood After Transplantation. FIG. 2 shows that the percentage of $CD34^+$, $c-Kit^+$, $Thy-1^+$ and $Sca1^+$ cells in peripheral blood was significantly increase in AMD treated animals compared to control animals after liver transplantation.

Figure 3:
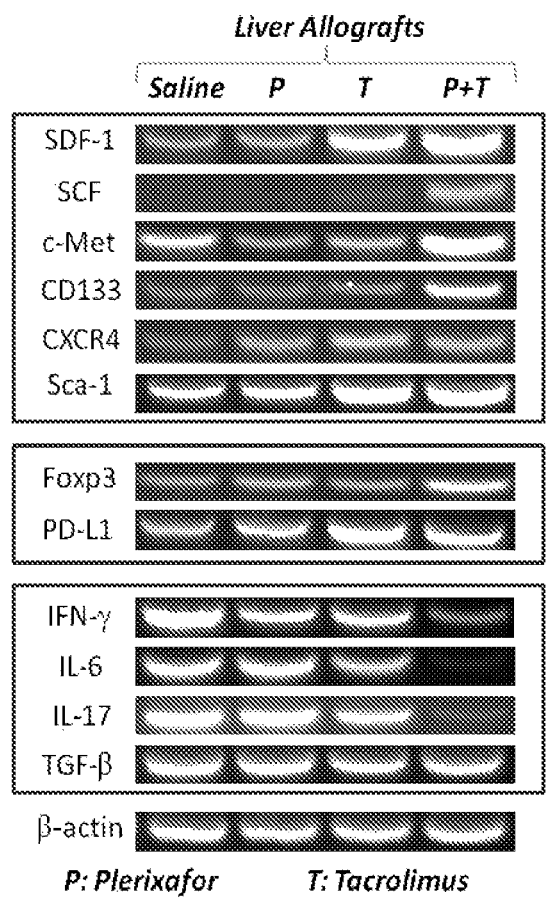
FIG. 3 displays PCR analysis of mRNA expression of SDF-1, SCF, c-Met, as well as Foxp3 in AMD plus low dose FK-506 group compared to other groups at day 7 post partial liver transplantation (PLT).

A Combination of AMD and Low Dose FK-506 Increased Not Only the Expression of Stem Cell Factors But Also Foxp3 (T-Regulatory Marker) in Liver Allografts and Spleens. PCR analysis shows the mRNA expression of SDF-1, SCF, c-Met, as well as Foxp3 were significantly increased in AMD plus low dose FK-506 group compared to other groups at day 7 after transplantation (FIG. 3).

Figure 4:
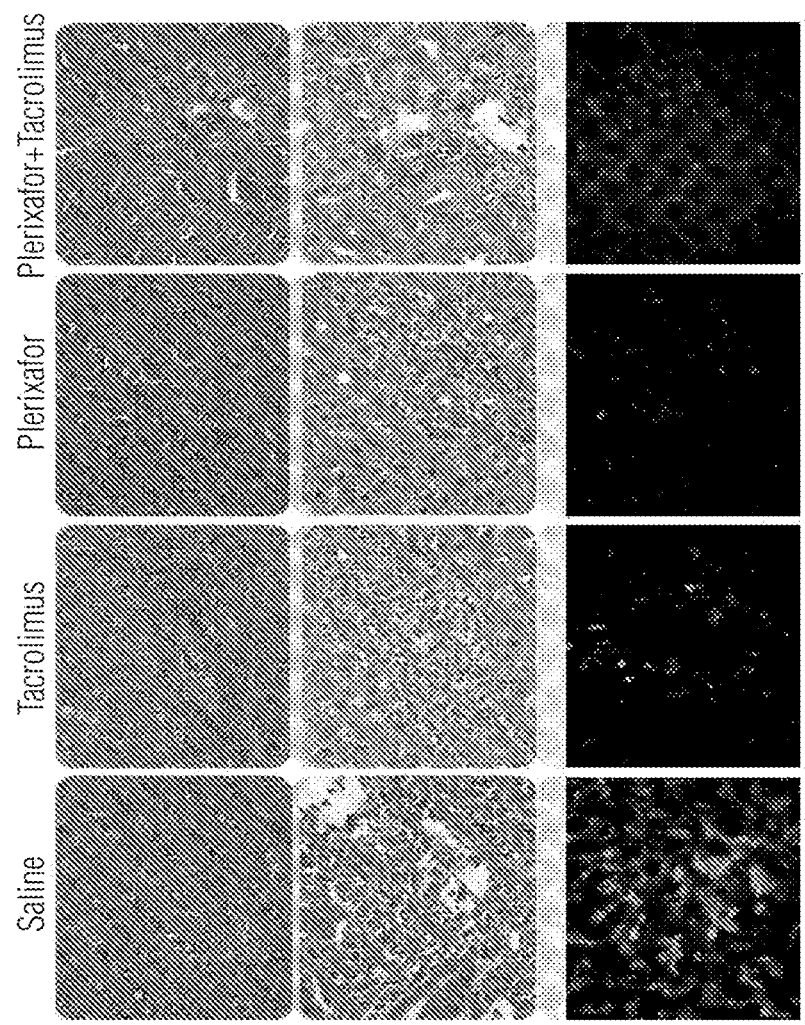
FIG. 4 shows hematoxylin and eosin (H&E) staining results of small DA liver transplanted into GFP-Lewis recipient rates, day 7 post PLT.

A Combination of AMD and Low Dose FK-506 Increases Recipient Derived Cells and Reduced Inflammatory Infiltration in Liver Allografts on Day 7 After Transplantation. H&E staining shows that in acute rejecting liver allografts 7 days after transplantation, heavy mononuclear cellular infiltration was preset in the expanded portal areas with disruption of liver architecture. The pattern of cellular infiltration was similar in the AMD or low dose FK-506 treated groups, but the number of infiltrating cells were less (FIG. 4 upper and middle panels). In contrast, there were much fewer inflammatory cells in portal areas in the AMD plus low dose FK-506 treated group. Interestingly, there were much more recipient derived GFP positive cells appeared in the parenchyma of liver allografts in AMD plus low dose FK-506 treated group compared to AMD or FK-506 alone group on day 7 after transplantation (FIG. 4, lower panels). These results suggest that a combination of AMD and low dose FK treatment not only reduces acute rejection, but also promotes the repopulation of liver allografts by recipients.

Mobilizing of Stem Cells in Recipients with Low Dose Immunosuppression Induces Long-Term Liver Allograft Acceptance and Prolongs the Survival of Skin Allograft from the Same Donor. In the control group, liver allografts were rejected within 12 days after transplantation. AMD or low dose FK-506 treatment did not significantly prolong the recipient survival although one of five recipients treated with FK-506 survives for more than 1 month. Interestingly, a combination of AMD and low dose FK-506 treatment induced long-term allograft acceptance (tolerance) without side effects. In these liver acceptance animals, skin allograft from same donor can survive for more than one month after transplantation.

Conclusion

Mobilization of recipient bone marrow stem cells by AMD promotes liver allograft acceptance and a combination of AMD and low dose immunosuppressant induces long-term allograft acceptance without side effects. Bone marrow stem cell mobilizing agents can be used for induction of organ transplant tolerance.

Supplemental Detailed Data

The present inventors hypothesized that mobilization of recipient bone marrow stem cells will facilitate a rapid repopulation of liver allografts in the acute rejection model and reduce or eliminate the need for immunosuppression. To test this hypothesis, liver transplants from dark agouti (DA) rats into Lewis rats, i.e. the rejection model were performed. Recipient rats were treated with a hematopoietic stem cell mobilizer (plerixafor) and/or low dose immunosuppressant (tacrolimus). Transplanted rats were divided into four groups: 1) a control group treated with saline), 2) treatment with low dose immunosuppressant (tacrolimus, 0.1 mg/kg/day), 3) stem cell mobilizer (plerixafor (AMD3100), 1 mg/kg/day) alone, or 4) a combination of low dose tacrolimus and plerixafor.

In small liver transplantation rats, plerixafor and/or tacrolimus were injected subcutaneously immediately after reperfusion and on days 1, 2, 3 and 7 following transplantation. In whole liver transplantation rats, plerixafor and/or tacrolimus were injected subcutaneously immediately after reperfusion and on days 1, 2, 3, 7, 10 and 15 following transplantation. Animals from each group were sacrificed on post-op days 3, 7 and 10 and liver tissue, spleen and peripheral blood were collected.

Figure 5B:
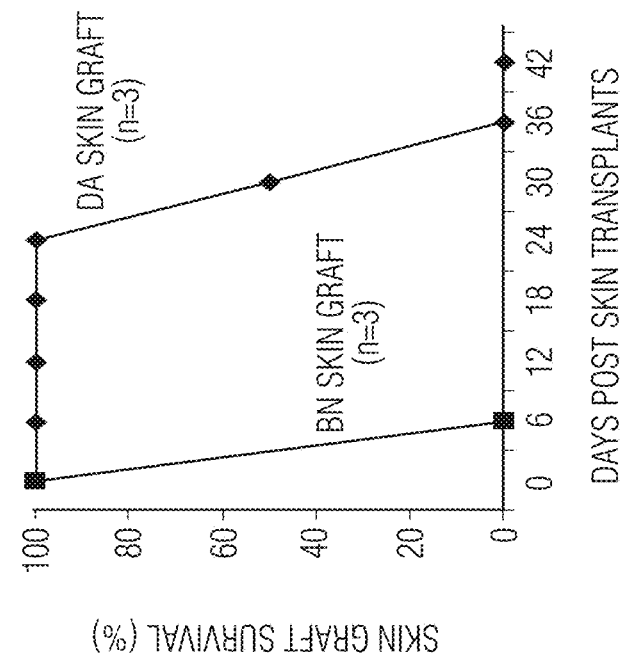
FIG. 5A-B present the survival results in the acute rejection model (DA into Lewis rats)
Figure 5A:
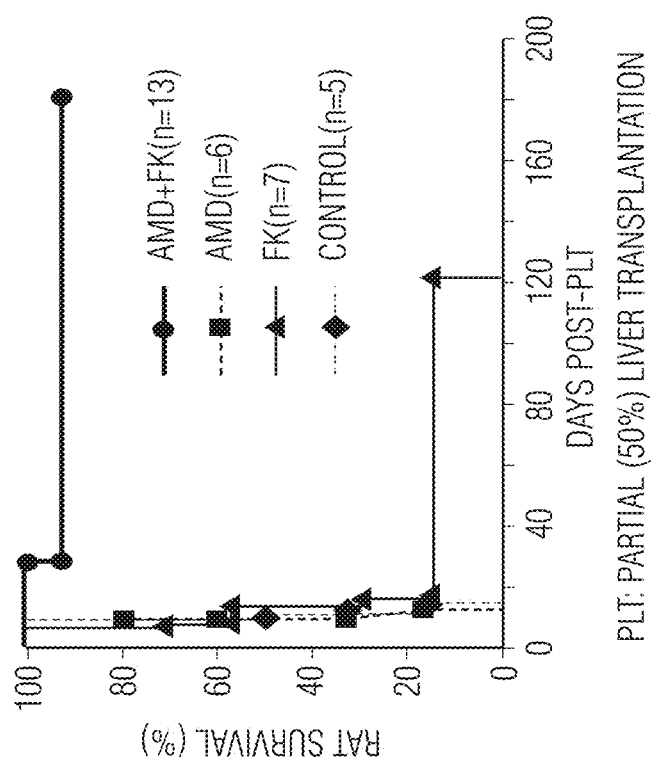

Effective Mobilization of Recipient BMD Stem Cells with Low Dose IS and Plerixafor Induces Long-Term Small Liver Allograft Acceptance and Prolongs the Survival of a Skin Allograft from the Same Donor. FIG. 2 shows that the percentage of $CD34^+$, $c-Kit^+$, $Thy-1^+$ and $Sca1^+$ cells in peripheral blood was significantly increased in plerixafor treated animals compare to control animals after liver transplantation. In the control group, as previously, liver allografts were all rejected within twelve days after transplantation. Treatment with plerixafor or low dose tacrolimus alone did not significantly prolong recipient survival (although one of five recipients treated with low dose tacrolimus alone survived 4 months). Interestingly, the combination of plerixafor and low dose tacrolimus treatment induced long-term (>6 months) allograft acceptance without obvious side effects (FIG. 5A). In these animals, a subsequent skin allograft from the same donor strain survived for more than one month following transplantation (FIG. 5B) while the skin allograft from Brown-Norway (BN) rats (third party) were rejected in 6 days suggesting donor specific non-responsiveness.

A Combination of Plerixafor and Low Dose Tacrolimus Increases Recipient Derived Cells and Reduces Inflammatory Infiltrate in Liver Allografts on Day Seven After Transplantation. H&E staining shows that in control group liver allografts undergoing acute rejection seven days after transplantation, heavy mononuclear cellular infiltration was present in expanded portal areas with disruption of liver architecture. This pattern of cellular infiltration was similar in the plerixafor or low dose tacrolimus treated animals, but the number of infiltrating cells was reduced (FIG. 4, upper and middle panels). In contrast, there were far fewer inflammatory cells in the portal areas of animals treated with both plerixafor and tacrolimus. Interestingly, there were many more recipient-derived GFP-positive cells in the parenchyma of liver allografts of animals that got both drugs compared to single drug treatment on day 7 after transplantation (FIG. 4, lower panels).

Figure 6:
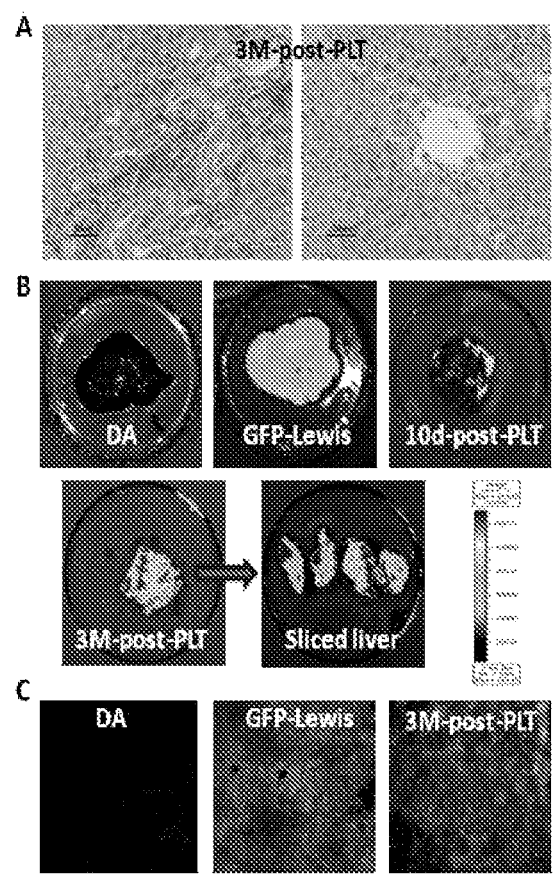
FIG. 6 shows green fluorescence protein imaging at 3 months post liver transplantation.

Three months after transplantation, FIG. 6A shows the bile duct regeneration and many small size hepatocytes in the central vein areas. GFP whole-organ fluorescence was measured using the Xenogen system. As shown in FIG. 6B, the donor DA liver has no GFP expression, as expected. However, the transplanted donor liver graft shows a high degree of fluorescence at three months after transplant into a GFP-Lewis recipient that was treated with plerixafor and tacrolimus. Fluorescent microscopy confirmed these findings (FIG. 6C). These results suggest that a combination of plerixafor and tacrolimus treatment not only reduced acute rejection, but also promoted the repopulation of liver allografts by mobilized recipient stem cells.

Treatment with Plerixafor and Tacrolimus Increases Expression of Stem Cell Factors as well as Foxp3 Staining (a Marker of Regulatory T Cells) in Liver Allografts and Spleens. PCR analysis shows that mRNA expression of SDF-1, SCF, c-Met, CD133 as well as Foxp3 were significantly increased in the dual treatment group compared to all other groups at day 7 after transplantation (FIG. 3). Interestingly, IFN-γ (a cytokine of Th1), IL-17 (a cytokine of Th17) as well as IL-6 (a promoter of Th17 development) were significantly decreased in the dual treatment group, although TGF-β (which is needed for both iTreg and Th17 development) remained the same.

Figure 7:
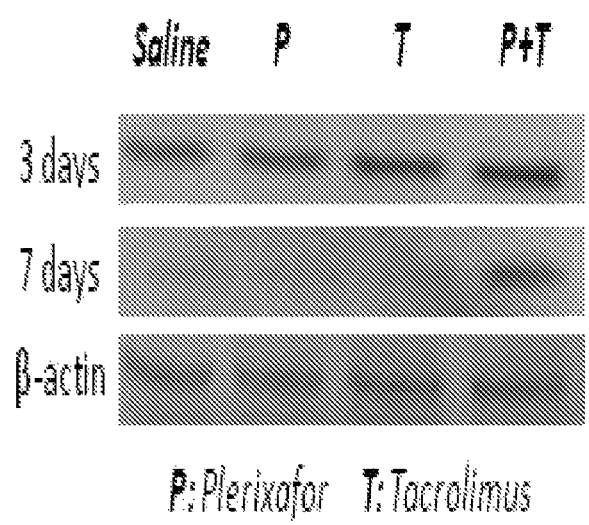
FIG. 7 shows SDF expression in small liver grafter after transplantation (DA into Lewis rats).

SDF-1 protein expression was further determined by western blot analysis. FIG. 7 shows that the levels of SDF-1 in liver allografts recovered from animals in the plerixafor plus tacrolimus group were significantly higher compared to other groups, especially at 7 days after transplantation.

Figure 8:
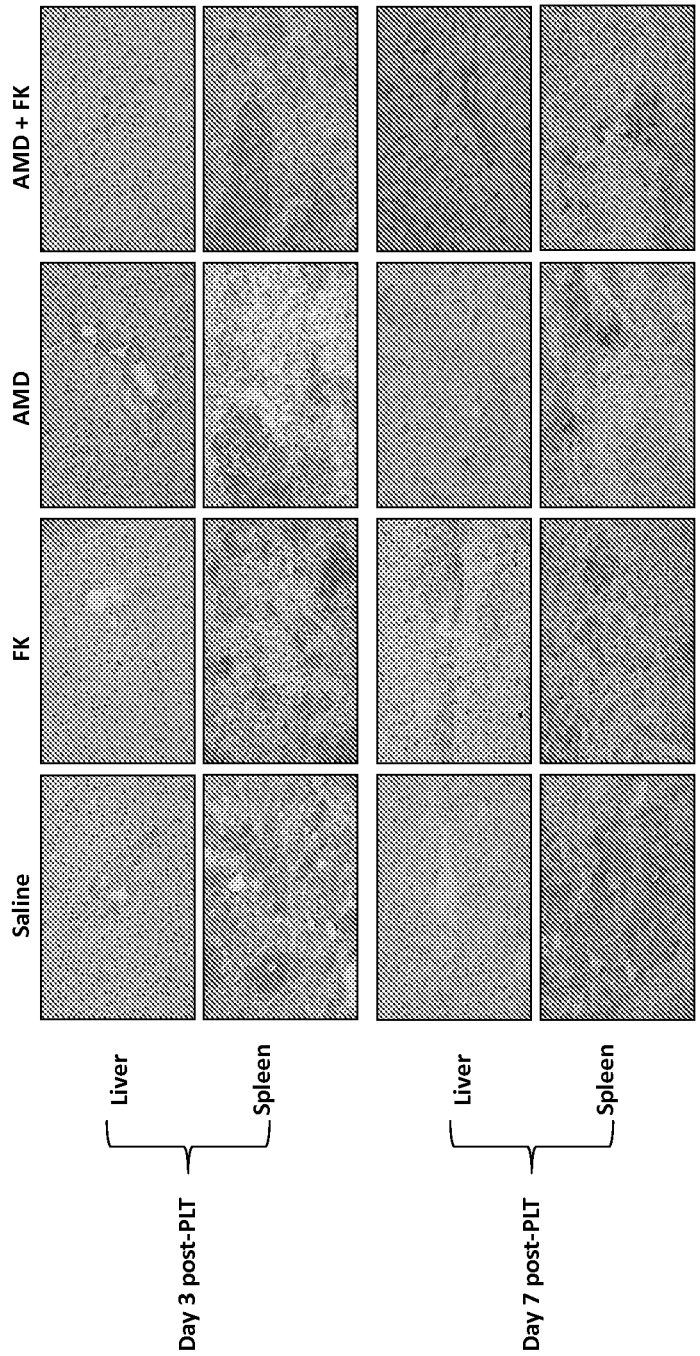
FIG. 8 presents immunohistochemistry staining results aimed at the detection of $CD133^+$ stem cells in liver allografts and spleens at days 3 and 7 after transplantation.
Figure 9:
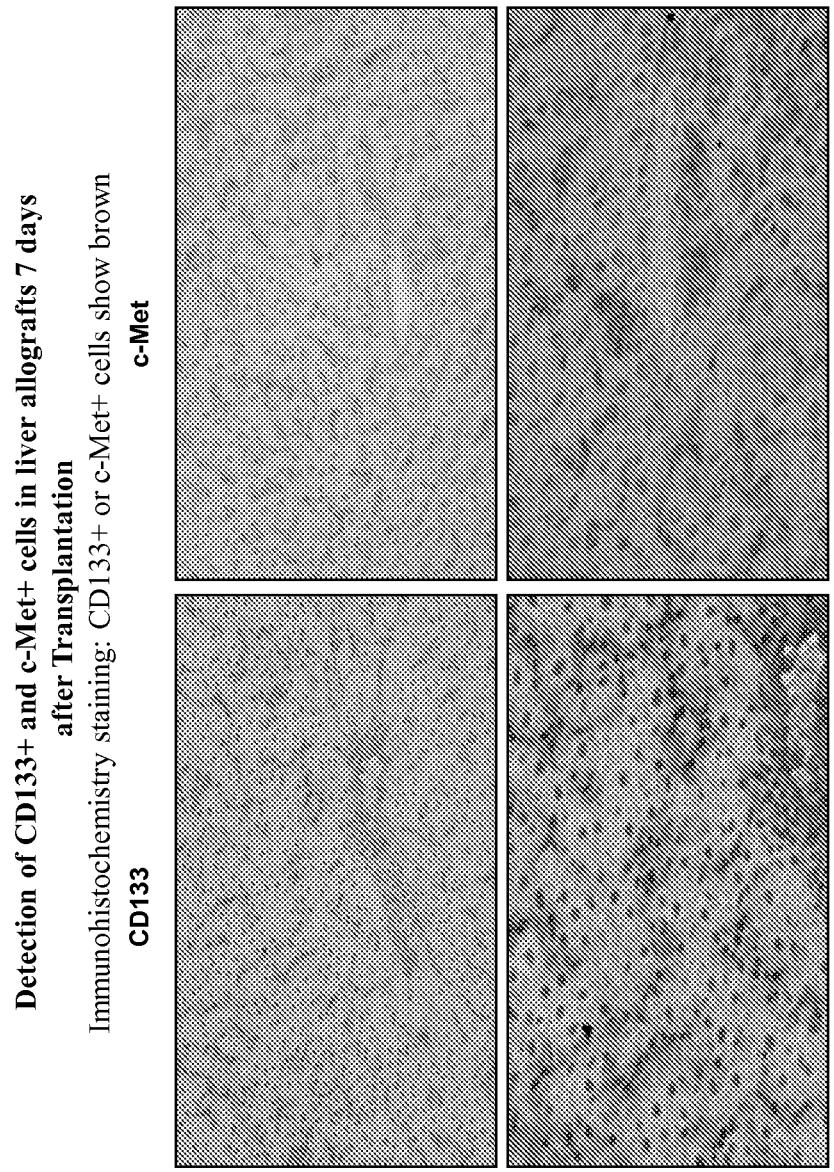
FIG. 9 presents immunohistochemistry staining results aimed at the detection of $CD133^+$ and $c\text{-}Met^+$ cells in liver allografts 7 days after transplantation.

Immunohistochemistry (IHC) staining showed that the number of CD133$^+$ cells in liver and spleen tissue sections from the dual treatment group was significantly increased at day 3 and 7 after transplantation (FIG. 8). Similarly, the number of c-Met$^+$ cells was also increased in the dual treatment group. Interestingly, patterns of staining of CD133 and c-Met in liver tissue sections were similar suggesting that these markers may stain many of the same cells (FIG. 9).

Figure 10:
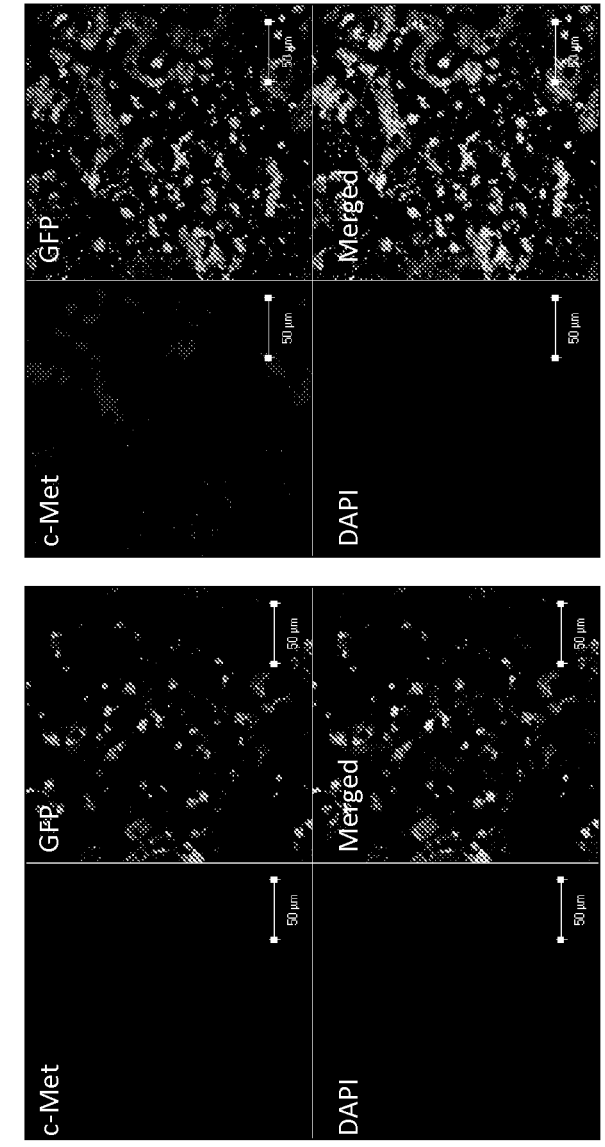
FIG. 10 shows immunofluorescent staining results aimed at the detection of recipient phenotype $c\text{-}Met^+$ cells in liver allografts 7 days after transplantation.
Figure 11:
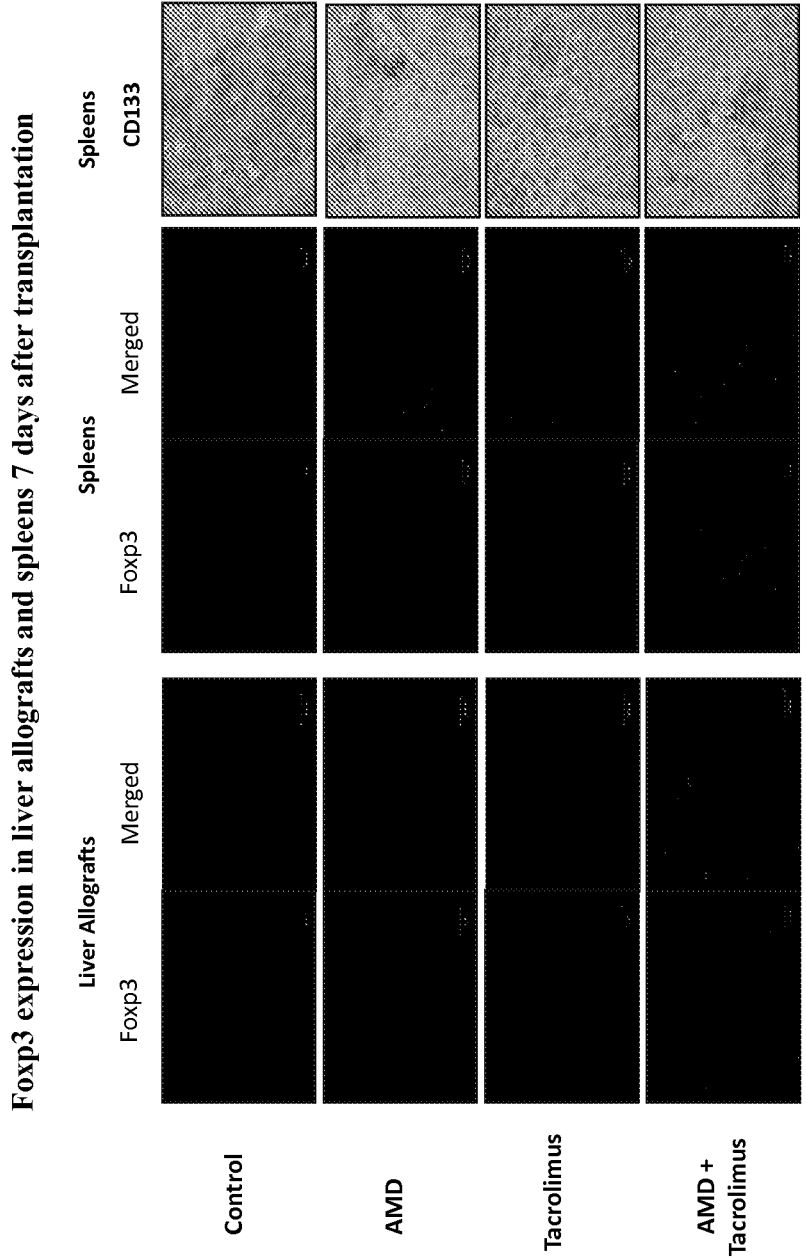
FIG. 11 shows immunofluorescent staining results from experiments detecting Foxp3 expression in liver allografts and spleens 7 days after transplantation.

The number of recipient (GFP$^+$)-derived c-Met positive (red) cells determined by immunofluorescence staining was significantly higher in tissue sections from liver and spleens in the dual treatment group compare to control animals after transplantation (DA into GFP transgenic Lewis) (FIG. 10). Immunofluorescence staining also showed that the number of Foxp3 positive cells was significantly higher in tissue sections from liver allografts and spleens in the dual treatment group (FIG. 11).

These results suggest that treatment with plerixafor and tacrolimus (low dose) facilitates stem cell mobilization and migration to liver allografts via increased expression of SDF-1, and may also promote the differentiation of Foxp3$^+$ regulatory T cells. It is very likely that the present invention (activation of regulatory T cells via mobilizing bone marrow stem cells) can be also used in other organ transplantation, such as kidney, pancreas, heart, lung, hands and faces.

Figure 12:
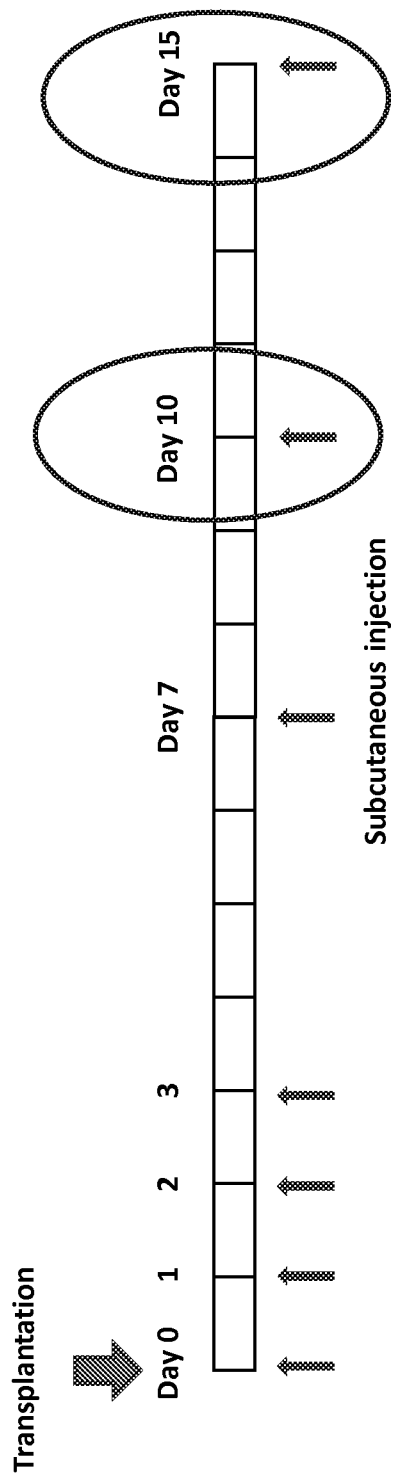
FIG. 12 presents the experimental protocol used for whole liver transplantation.
Figure 13:
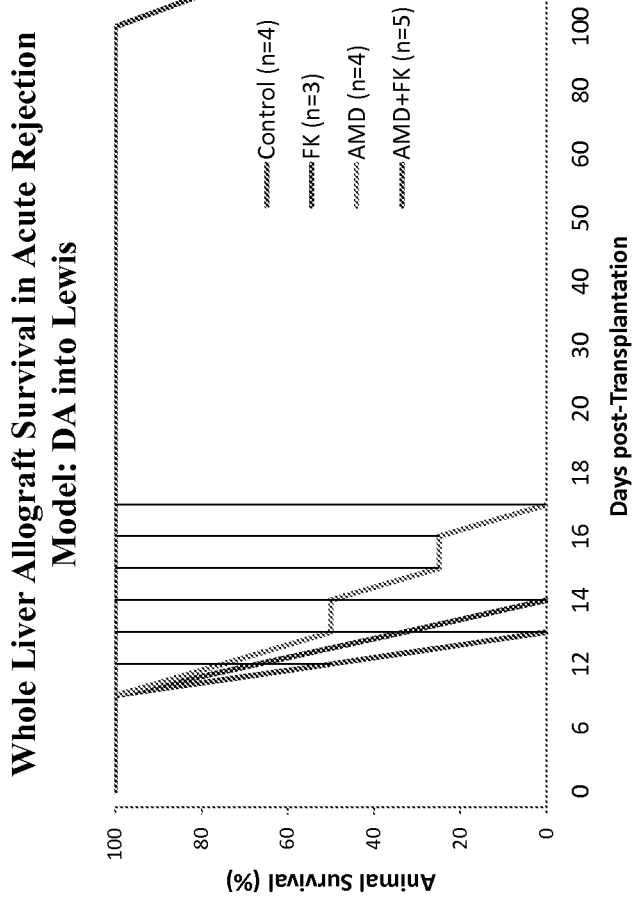
FIG. 13 presents the whole liver allograft survival results in the acute rejection model (DA into Lewis rats).

A Combination of Plerixafor and Low Dose Tacrolimus Treatment Induces Whole Liver Allograft Acceptance. In whole liver transplantation rats, plerixafor and/or tacrolimus were injected subcutaneously immediately after reperfusion and on days 1, 2, 3, 7, 10 and 15 following transplantation (FIG. 12). FIG. 13 shows that in the control group, liver allografts were all rejected within twelve days after transplantation. Treatment with plerixafor or low dose tacrolimus alone did not significantly prolong recipient survival. Interestingly, the combination of plerixafor and low dose tacrolimus treatment induced long-term (>4 months) allograft acceptance without obvious side effects.

Example 2

Induction of Kidney Allograft Acceptance by Mobilizing Bone Marrow Stem Cells

Materials and Methods

Rat Strains and Care. DA (RT1A$^a$) rats were purchased from Harlan ague-Dawley (Indianapolis, Ind.) and used at 8-12 weeks of age. The green fluorescent protein (GFP) transgenic Lewis (RT1$^1$) rat strain was obtained from the National Institutes of Health (NIH)-funded Rat Resource and Research Center (RRRC), University of Missouri, Columbia, Mo. Animals were maintained in the specific pathogen-free facility of Johns Hopkins Medical Institutions. Animals were cared for according to NIH guidelines and under a protocol approved by the Johns Hopkins University Animal Care Committee.

Orthotopic Kidney Transplantation. An orthotopic kidney transplantation in rats was performed under isoflurane (Abbott Laboratories, North Chicago, Ill.) inhalation anesthesia according to the technique described by Daniller (1968). Specifically, the DA to Lewis model of acute rejection was studied. Briefly, donor kidneys obtained from male DA rats were flushed with 10 ml cold saline and were stored at 4° C. while the recipient to be prepared. Total cold ischemic time was no longer than 40 minutes. Lewis male recipients were transplanted following left native nephrectomy. The donor renal artery, vein and ureter were anastomosed to the recipient renal artery, vein and ureter. The anastomosis was completed using 10-0 silk sutures. The right native kidney was removed before closing the abdomen.

Experimental Groups and Animal Treatment. Transplanted rats were divided by four groups including control group (treated with same volume of saline), low dose of immunosuppressant (FK-506, 0.05 mg/kg/day), stem cell mobilizer (AMD3100, 1 mg/kg/day) and a combination of low dose FK-506 and AMD3100. AMD3100 were injected subcutaneously immediately after reperfusion (day 0) and day 2, 4 and 6 following kidney transplantation. FK-506 were injected subcutaneously immediately after reperfusion (day 0) and day 1, 2, 3, 4, 5, 6 and 7 following transplantation. Treatments were repeated in combination treated group at 1, 2 and 3 months after transplantation. Some of animals were sacrificed at day 7 and 30 after transplantation and kidney tissue, spleen and peripheral blood were collected.

Flow Cytometry. Single-cell suspensions (5×10$^5$) of peripheral blood monocytes were analyzed for lineage negative CD34, CD133, Thy 1, and c-Kit expression. Nonspecific antibody binding was blocked with goat and rat serum (Sigma) for 30 minutes.

Histological Studies. Histological changes in kidney tissue sections were evaluated by H&E staining, Recipient-derived GFP positive cells in kidney tissue sections were analyzed by fluorescence microscopy.

Xenogen Imaging Analysis for Kidney Allografts. Green fluorescence protein (GFP) expression in kidney allografts were analyzed by Xenogen Imaging system.

Results

Figure 14:
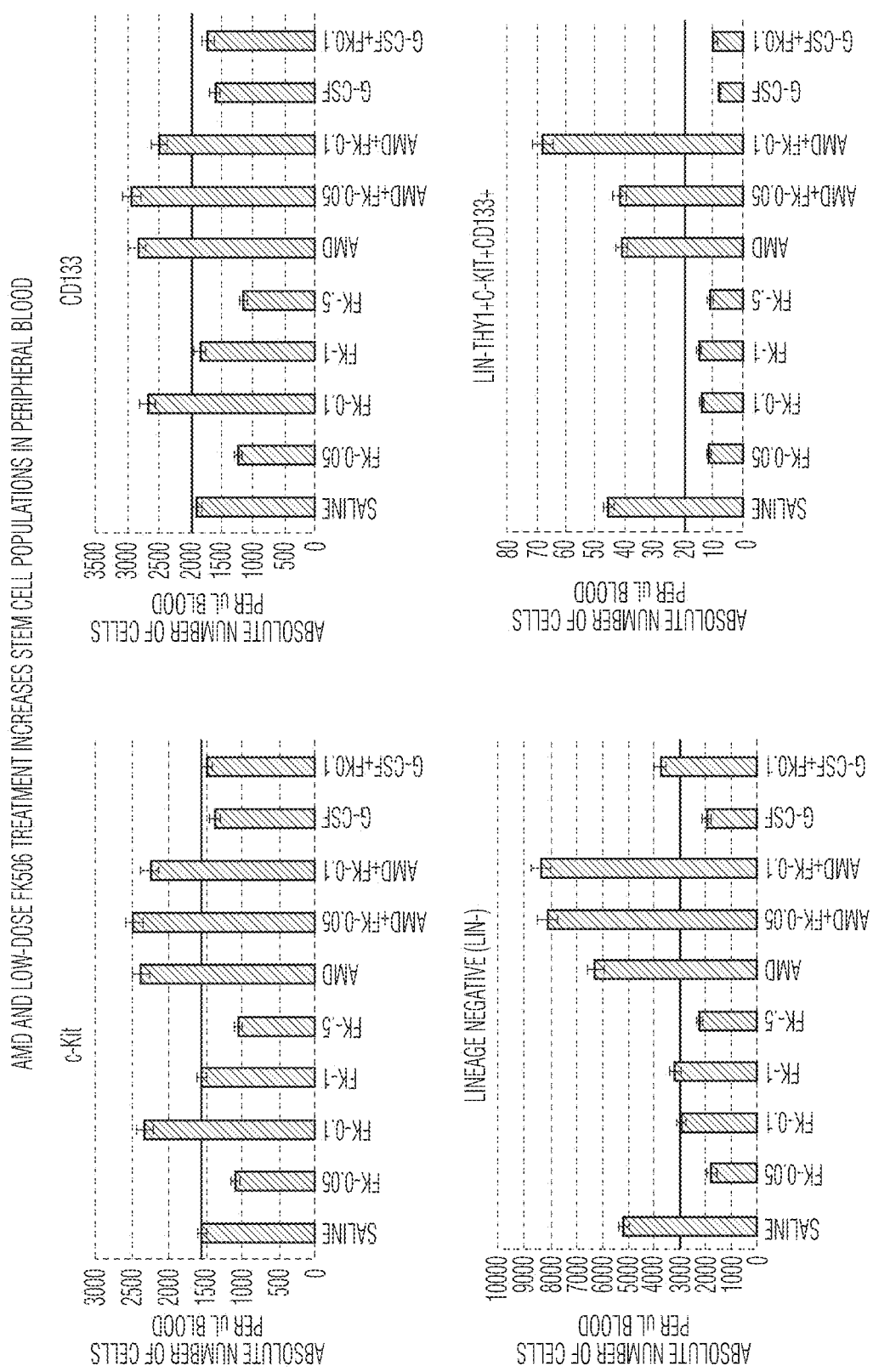
FIG. 14 shows that the absolute number of $c\text{-}Kit^+$, $CD133^+$ or lineage negative ($Lin^-$) and $Thy1^+c\text{-}Kit^+CD133^+$ triple positive cells in peripheral blood was significantly increased in AMD treated animals compare to saline or G-CSF treated animals.

AMD And Low-Dose FK Treatment Significantly Increases Stem Cell Populations In Peripheral Blood. Peripheral blood cells were isolated from animals at 3 hours after injection with AMD and/or FK. Complete blood count (CBC) was measured and stem cell markers were quantified by flow cytometry. The absolute number of stem cells was calculated as WBC (-thous./μL)×% of stem cells. FIG. 14 shows that the absolute number of c-Kit$^+$, CD133$^+$ or lineage negative (Lin$^-$) and Thy1$^+$c-Kit$^+$CD133$^+$ triple positive cells in peripheral blood was significantly increased in AMD treated animals compare to saline or G-CSF treated animals. Surprisingly, low-dose FK (0.1 mg/kg) but not high dose FK treatment significantly increases c-Kit+ and CD133$^+$ cells in peripheral blood. Interestingly, the elevation of Lin$^-$ and Thy1$^+$c-Kit$^+$CD133$^+$ cells was more dramatically in animals treated with a combination of AMD and low dose FK-506. These results suggest a synergistic role of AMD and low-dose FK-506 in mobilization of bone marrow stem cells.

Figure 15:
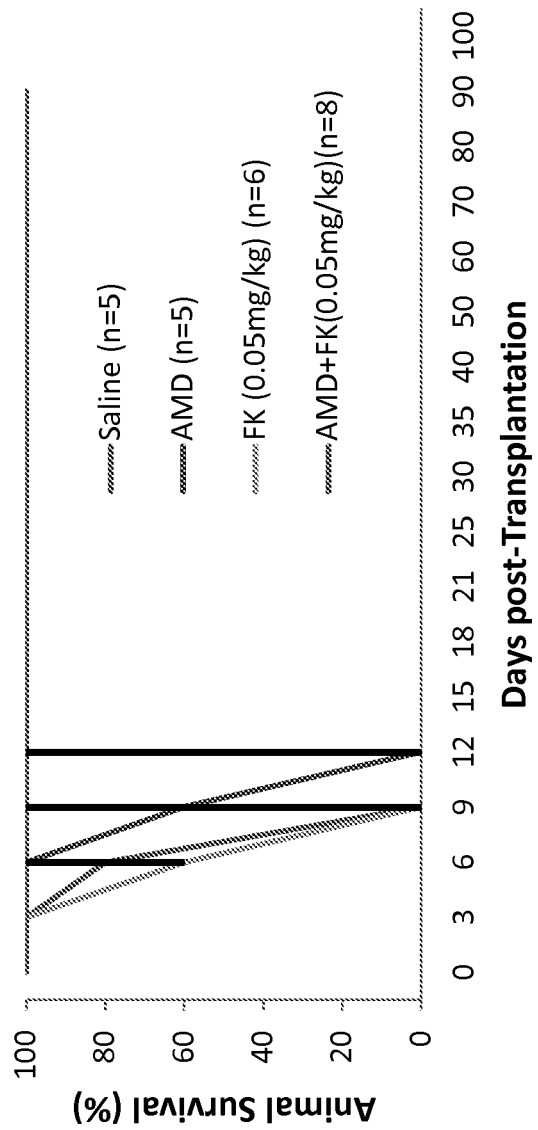
FIG. 15 shows that treatment with AMD3100 and Tacrolimus induces long-term kidney allograft acceptance.

Mobilizing Of Stem Cells In Recipients With AMD And Low Dose FK-506 Induces Long-Term Kidney Allograft Acceptance. In control group (FIG. 15), kidney allografts were rejected within 10 days after transplantation. AMD or low dose FK (0.05 mg/kg) treatment did not prolong the recipient survival. Interestingly, a combination of AMD and low dose FK-506 (0.05 mg/kg) treatment induced long-term allograft acceptance without side effects. All recipients (100%) treated with AMD and low-dose FK survive for more than three months.

Figure 16A:
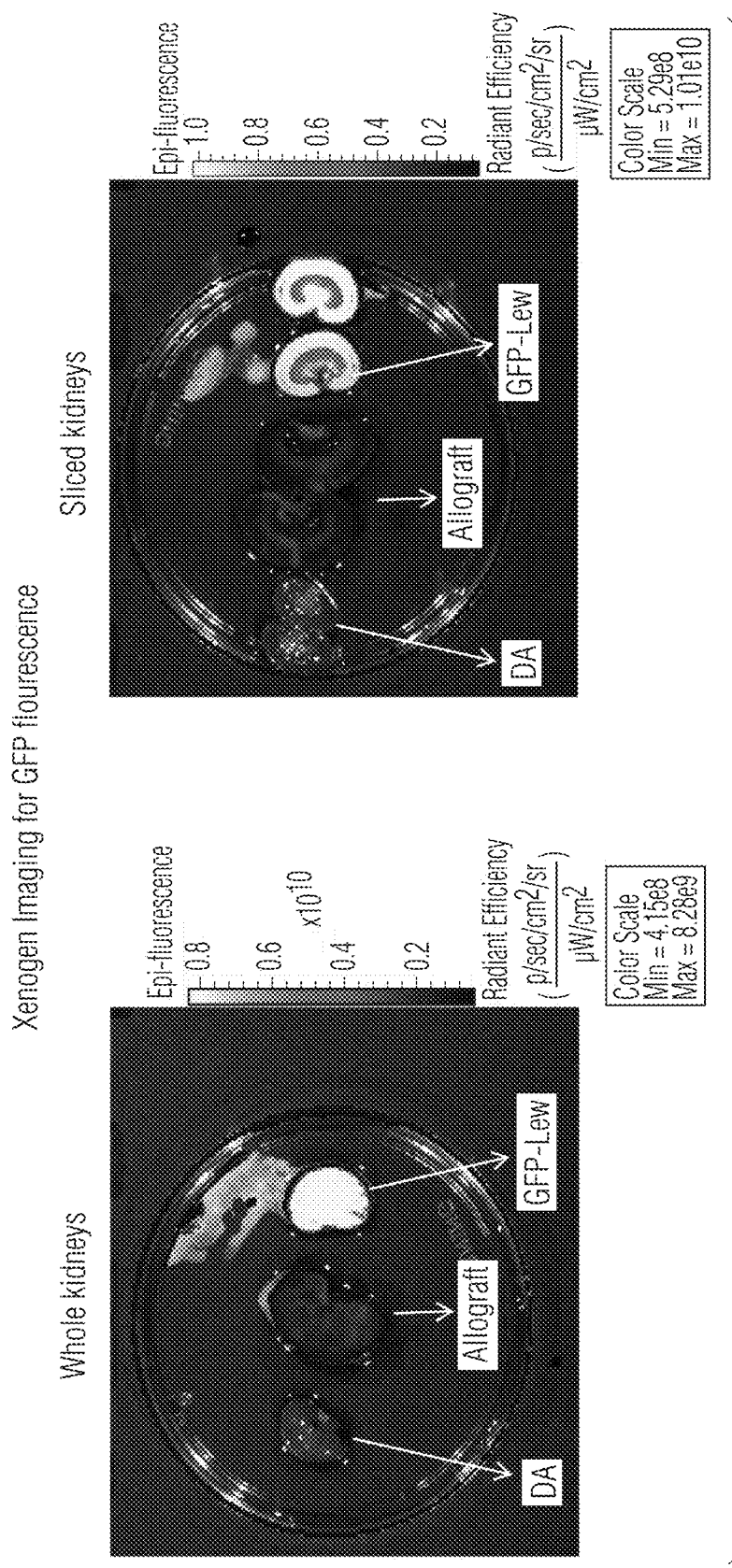
FIG. 16A-B demonstrates that a combination of AMD3100 and Tacrolimus promotes the repopulation of kidney allografts by recipient derived cells.
Figure 16B:
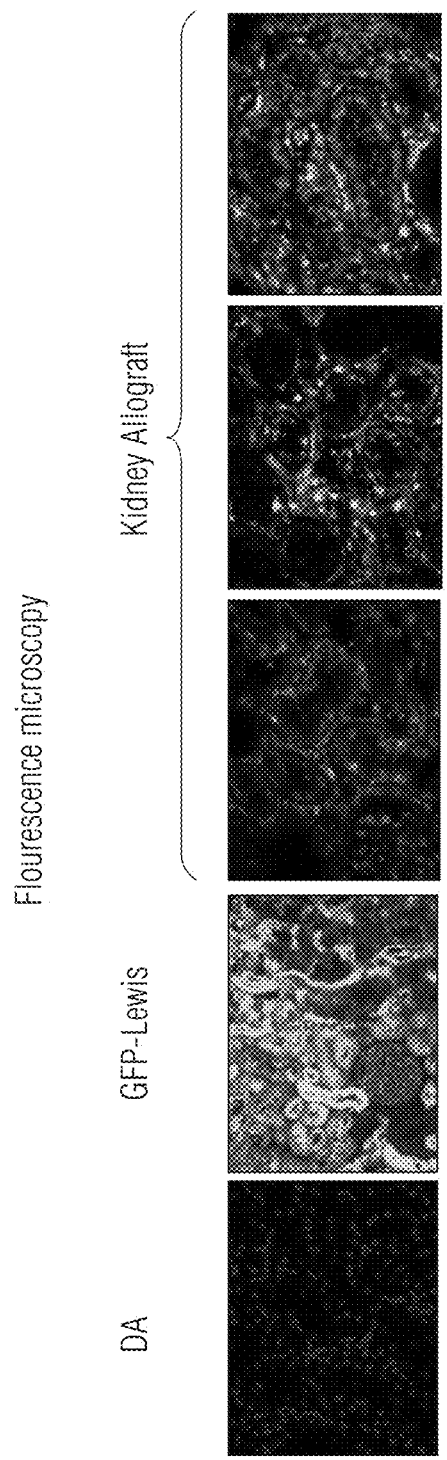
Figure 17:
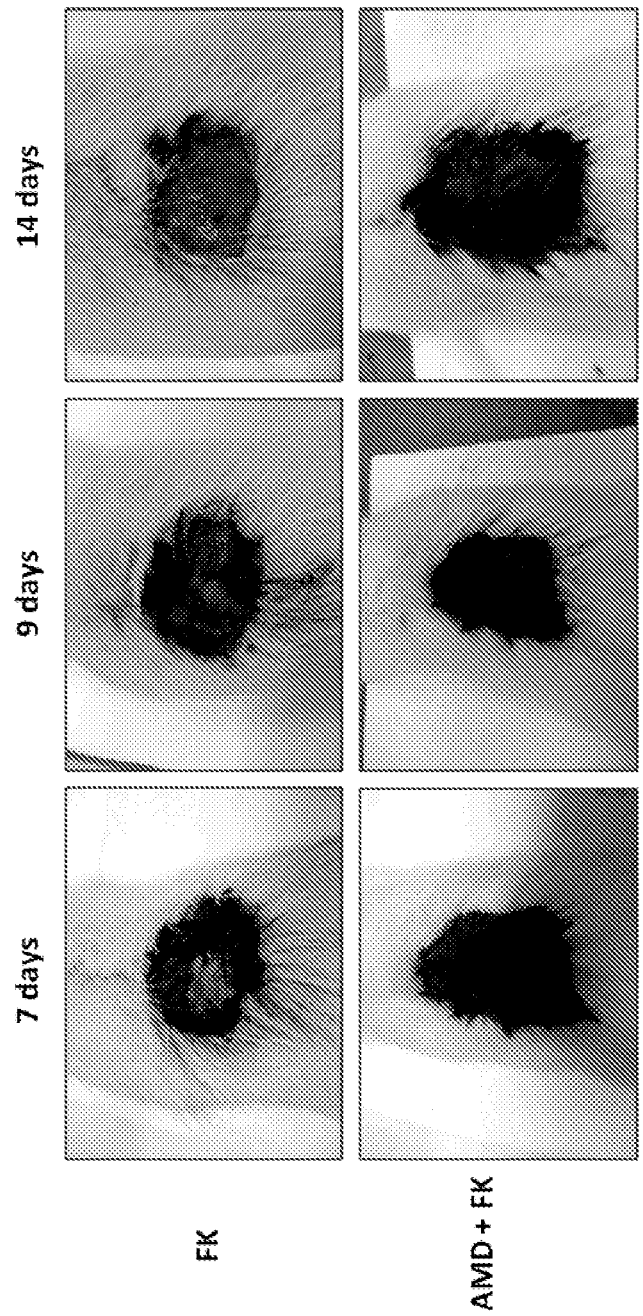
FIG. 17 shows skin xenograft survival results of mouse into rat.

A Combination Of AMD And Low Dose FK-506 Promotes The Repopulation Of Kidney Allografts By Recipient Derived Cells. Kidneys from DA rats were transplanted into GFP-Lewis recipients. GFP whole-organ fluorescence was measured using the Xenogen system. As shown in FIG. 16, the donor DA kidney has no GFP expression, as expected. However, the transplanted donor kidney graft showed a high degree of fluorescence at 1 month after transplant into a GFP transgenic Lewis recipient that was treated with AMD and tacrolimus (0.1 mg/kg). Although recipient inflammatory cells could have accounted for this, it was found that recipient-derived GFP positive cells appeared in the tubules of allograft and tubule epithelial cells themselves were GFP positive. These results suggest that recipient-derived stem cells are able to help regenerate tubules and a combination of AMD and low dose FK treatment not only reduces acute rejection, but also promotes the repopulation of kidney allografts by recipients.

Conclusion

Mobilization of recipient bone marrow stem cells by AMD promotes kidney allograft acceptance and a combination of AMD and low dose Tacrolimus induces long-term kidney allograft acceptance without side effects. Bone marrow stem cell mobilizing agents can be used for induction of kidney transplant tolerance.

Example 3

Induction of Skin Allograft Acceptance by Low Dose Immunosuppression and Mobilizing Bone Marrow Stem Cells Allogenic skin has had a major role in acute burn care for over 100 years, and is the gold standard for temporary skin substitutes. The major obstacle to prolonged use is its immunogenicity.

Based on the data described herein, it is further hypothesized that mobilization of recipient bone marrow stem cells will facilitate a repopulation of skin allografts with recipient-derived cells and reduce or eliminate the need for immunosuppression in this population of patients where infection plays a major role in mortality. To test this hypothesis, skin transplants were performed from DA rats to Lewis rats, and recipient rats were treated with stem cell mobilizer (mozobil: AMD3100) and/or low dose immunosuppressant (Tacrolimus, FK-506).

Materials and Methods

Rat Strains and Care. DA (RT1A$^a$) rats and C57/B6 mice were purchased from Harlan ague-Dawley (Indianapolis, Ind.) and used at 8-12 weeks of age. The green fluorescent protein (GFP) transgenic Lewis (RT1$^1$) rat strain was obtained from the National Institutes of Health (NIH)-funded Rat Resource and Research Center (RRRC), University of Missouri, Columbia, Mo. Animals were maintained in the specific pathogen-free facility of Johns Hopkins Medical Institutions. Animals were cared for according to NIH guidelines and under a protocol approved by the Johns Hopkins University Animal Care Committee.

Skin Transplantation. DA rats or C57/B6 mice were used as skin donors and GFP transgenic Lewis rats were used as recipients. A graft bed (2.5×3 cm) was prepared on the back of a recipient rat; special care was given to preserving the panniculus carnosus. A 2.5×3 cm$^2$ graft, which had been prepared from the body trunk of a donor, was transplanted with interrupted sutures of 5-0 silk. The graft was covered with a protective tape and the first inspection was conducted 2 days after skin grafting and was followed by daily inspection. The rejection was defined as the day when the skin graft developed a red-brown color and hard consistency.

Experimental groups and animal treatment. Transplanted rats were divided by four groups including control group (treated with same volume of saline), low dose of immunosuppressant (FK-506, 0.1 mg/kg/day), stem cell mobilizer (AMD3100, 1 mg/kg/day) and a combination of low dose FK-506 and AMD3100. AMD3100 were injected subcutaneously immediately after transplantation and every two days following skin transplantation. FK506 were injected subcutaneously every day following transplantation.

Biopsies. At selected times, 2.0-mm full-thickness punch biopsies were taken for histologic evaluation of frozen and formalin samples and Xenogen imaging analysis of GFP expression.

Results

Mobilizing of Stem Cells in Recipients with AMD and Low Dose FK-506 Induces Long-Term Skin Allograft Acceptance and Prolongs Skin Xenograft Survival. In control group (Table 1), skin allografts were rejected within 7 days after transplantation. AMD or low dose FK (0.1 mg/kg) treatment did not significantly prolong the allograft survival.

Interestingly, a combination of AMD and low dose FK-506 (0.1 mg/kg) treatment induced long-term skin allograft acceptance without side effect. All skin allografts in recipients treated with AMD and low-dose FK survive for more than one month. Similarly, AMD or low-dose FK treatment did not prolong the xenograft survival. However, a combination of AMD and low-dose FK significantly prolonged the xenograft survival (Table 1 and FIG. 1).

TABLE 1

Skin Graft Survival

| Donors | Recipients | Treatment | Number | Graft Survival (days) |
|---|---|---|---|---|
| DA | Lewis | Saline | 3 | 6, 6, 7 |
|  |  | FK (0.1 mg/kg) | 3 | 7, 8, 9 |
|  |  | AMD (1 mg/kg) | 4 | 6, 7, 7, 8 |
|  |  | AMD + FK | 6 | >30 (6) |
| C57/B6 | Lewis | Saline | 3 | 5 (3), 6 |
|  |  | FK (0.1 mg/kg) | 3 | 5, 6, 6 |
|  |  | AMD (1 mg/kg) | 3 | 5 (2), 6 |
|  |  | AMD + FK | 4 | 17, 18 (2), 20 |

Figure 18B:
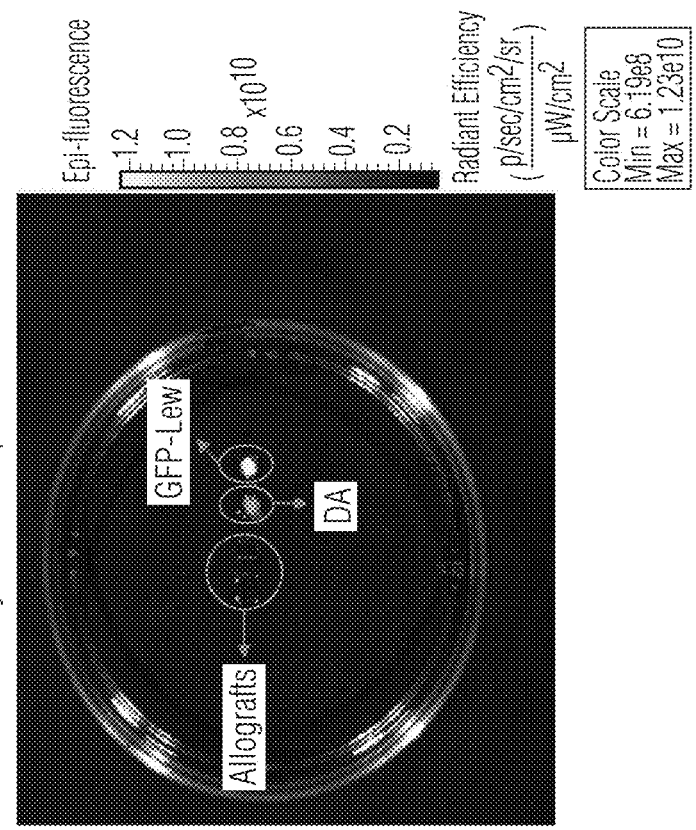
FIG. 18A-B present GFP expression data from skin graft experiments.
Figure 18A:
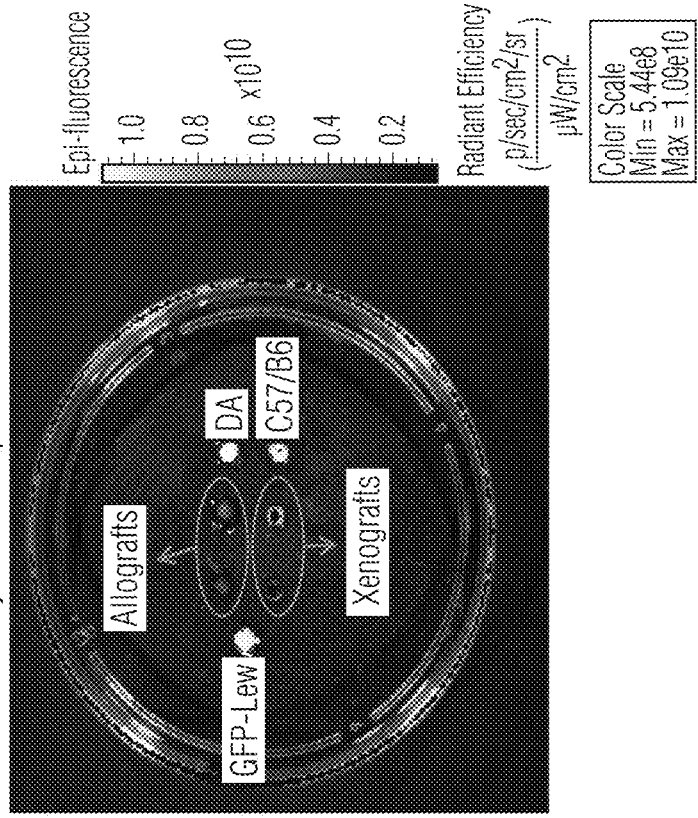
Figure 19:
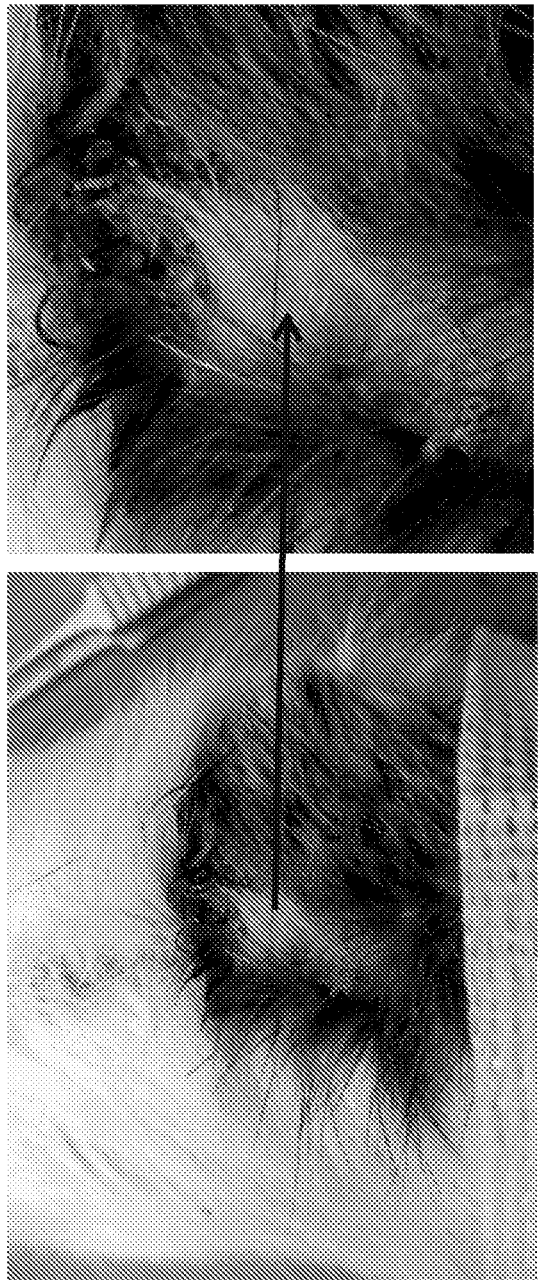
FIG. 19 shows repopulation of skin allograft by the recipient 36 days after transplantation.

A Combination of AMD and Low Dose FK-506 Promotes the Repopulation of Skin Grafts by Recipient Derived Cells. GFP fluorescence of skin biopsies was measured using the Xenogen system. As shown in FIG. 18A, the GFP recipient skin expresses strong fluorescence, and the donor DA or C57/b6 skin has no GFP expression, as expected. However, the transplanted donor skin graft shows a high degree of fluorescence at 7 days after transplant into a GFP transgenic Lewis recipient that was treated with AMD and tacrolimus (0.1 mg/kg). Interestingly, the degree of fluoresce in skin allografts is higher compared to xenografts. A high level of fluorescence remains in skin allografts at 28 days after transplantation (FIG. 18B). FIG. 19 shows a newly regenerated skin with white hair suggesting repopulation of skin allograft by recipient. These results suggest that recipient-derived stem cells are able to repopulate the skin graft and a combination of AMD and low dose FK treatment not only reduces acute rejection, but also promotes the repopulation of skin allografts by recipients.

Conclusion

Mobilization of recipient bone marrow stem cells by AMD and low-dose Tacrolimus promotes skin allograft acceptance and a combination of AMD and low dose Tacrolimus prolongs skin xenograft survival without side effects. Skin allografts can be repopulated by recipient derived cells. Bone marrow stem cell mobilizing agents can be used for induction of skin transplant tolerance.

Example 4

Treatment of Inflammatory Bowel Diseases

In one embodiment, the present invention relates to use of stem cell mobilizing agents and low dose immunosuppression, particularly in the form of combination for the treatment of inflammatory bowel diseases (IBD), and to using pharmacological stem cell mobilization strategies to promote mucosal healing in IBD as new therapeutic options. The combination of drugs significantly decreased the clinical and histologic severity of colonic inflammation and improved mucosal healing when administered to IL-10 knockout mice with established colitis or mice with dextran sulphate sodium (DSS)-induced colitis. These findings offer a significant therapeutic approach for patients with IBD.

The present embodiments are based, in part on the discovery that a low dose of the immunosuppressive drug FK-506 in combination with a stem cell mobilizing agent AMD3100 decrease the clinical and histologic severity of colonic inflammation, and improve mucosal healing (regeneration) when administered to IL-10 knockout mice with established colitis or acute mouse model of dextran sulphate sodium (DSS)-induced colitis.

The present example relates to use of FDA approved drugs—stem cell mobilizing agent AMD3100 (A) and low dose immunosuppressive drug FK-506 (F), particularly in the form of combination (AF) for the treatment of inflammatory bowel diseases (IBD), and to using pharmacological stem cell mobilization strategies to promote mucosal healing in IBD as new therapeutic options.

Inflammatory bowel diseases (IBD; Crohn's disease (CD), ulcerative colitis (UC)) are chronic relapsing diseases that lead to structural damage with destruction of the bowel wall. IBD represents a significant and rapidly growing healthcare burden in developed countries, and impacts the quality of life of millions of people. More than 1.5 million individuals in the USA and 2.2 million in Europe suffer from IBD (Am. J. Gastroenterol. 106(Suppl. 1), S2-S25; quiz S26 (2011), Immunity 34(3), 293-302 (2011)). Statistics published by the American College of Gastroenterology Task Force show that IBD is responsible for 2.3 million physician visits, 180,000 hospitalizations and costs US $6.3 billion per year (Am. J. Gastroenterol. 106(Suppl. 1), S2-S25; quiz S26 (2011)). Furthermore, over the long term, a large percentage of patients with IBD will require surgery for IBD-related complications, further adding to the socioeconomic impact of this disease(s). Currently, the available therapeutic approaches for IBD rely largely on generalized immunosuppression and are intended to induce remission and/or to prevent relapse; no treatment thus far has led to cure of these diseases. A regenerative medicine approach using cell based therapies is currently viewed as one of the most promising options on the horizon for the curative treatment of IBD (Regen. Med. (2013) 8(5), 631-644). Despite the encouraging results of recent clinical trials employing stem cell-based therapies as treatment for IBD, the complex, time consuming and expensive process needed to harvest, expand and transplant the cells makes it difficult to treat large numbers of patients.

Here, the present inventors tested the hypothesis that pharmacological mobilization of endogenous stem cells decrease the clinical and histologic severity of colonic inflammation and improve mucosal healing in mice with IBD.

Materials and Methods

Reagents. AMD3100 was obtained from Sigma-Aldrich (St. Louis, Mo.). Tacrolimus purchased from Pharmacy at Johns Hopkins hospital.

Experimental animals and establishment of DSS mouse colitis model. 6-7 week old weighing 18-21 g C57BL/6J mice at the begging of the experiment were used for establishment of DSS mouse colitis model as described previously (Inflammatory Bowel Diseases Volume 15, Issue 2, pages 261-274, February 2009). Mice were given drinking water and standard rodent pellets ad libitum. Briefly, colitis was induced by feeding 3% DSS (ICN Biomedicals Inc., Aoraro, Ohio, USA; molecular weight 36-50 kDa, dissolved in drinking water) ad libitum for seven days. Control mice for the DSS received the same drinking water without DSS. At day 10, following induction with DSS, animals were sacrificed and the entire colon and small intestine were quickly removed and photographed. Colon was immediately cleared of feces by gently flushing with ice-cold saline using a syringe. For histology, colonic segments taken were fixed in 10% neutral buffered formalin, embedded in paraffin and sectioned.

Disease activity index (DAI) of DSS-induced colitis. Clinical progress in DSS-induced colitic mice was monitored. Disease activity index (DAI) was calculated by: weight loss (0 point=none, 1 point=1-5% weight loss, 2 points=5-10% weight loss, 3 points=10-15% weight loss and 4 points-more than 15% weight loss), stool consistency/diarrhea (0 points=normal, 2 points=loose stools, but still formed, 3 points=very soft, 4 points=watery diarrhea), bleeding (0 points=no bleeding, 2 points=slight bleeding, 3 points=blood trace in stool visible, 4 points, gross bleeding (by ColoScreen occult blood test (Helena Laboratories, Beaumont, Tex.)). The sum of weight loss, diarrhea, and bleeding resulting in the total DAI score ranging from 0 (unaffected) to 12 (severe colitis).

IL-10-deficient murine model of inflammatory bowel disease. IL-10−/− mice on the C57BL/6 background (Jackson Laboratories, Bar Harbor, Me.) were housed under conventional conditions and allowed access to food and water ad libitum. The development of colitis was detected by daily observations of weight loss and stool consistency and by weekly stool tests for occult blood (Hemoccult Sensa II, Beckman Coulter, Palo Alto, Calif.). 4-5 month old weighing 17-24 g mice with IBD were used for this study. Animals were sacrificed at 4 weeks after drug treatment and colon tissues were collected.

The AF dual drug treatment. The animals were injected subcutaneously with a combination of AMD3100 (A) (1.0 mg kg-1, Sigma-Aldrich, St Louis, Mo.) and FK-506 (F) (0.1 mg kg-1, purchased from Pharmacy at Johns Hopkins hospital) every two days or same amount of saline.

Statistical analysis. Student's t test or analysis of variance (ANOVA) was used to compare differences between groups. A P value of 0.05 was considered to be statistically significant.

Results

Figure 20:
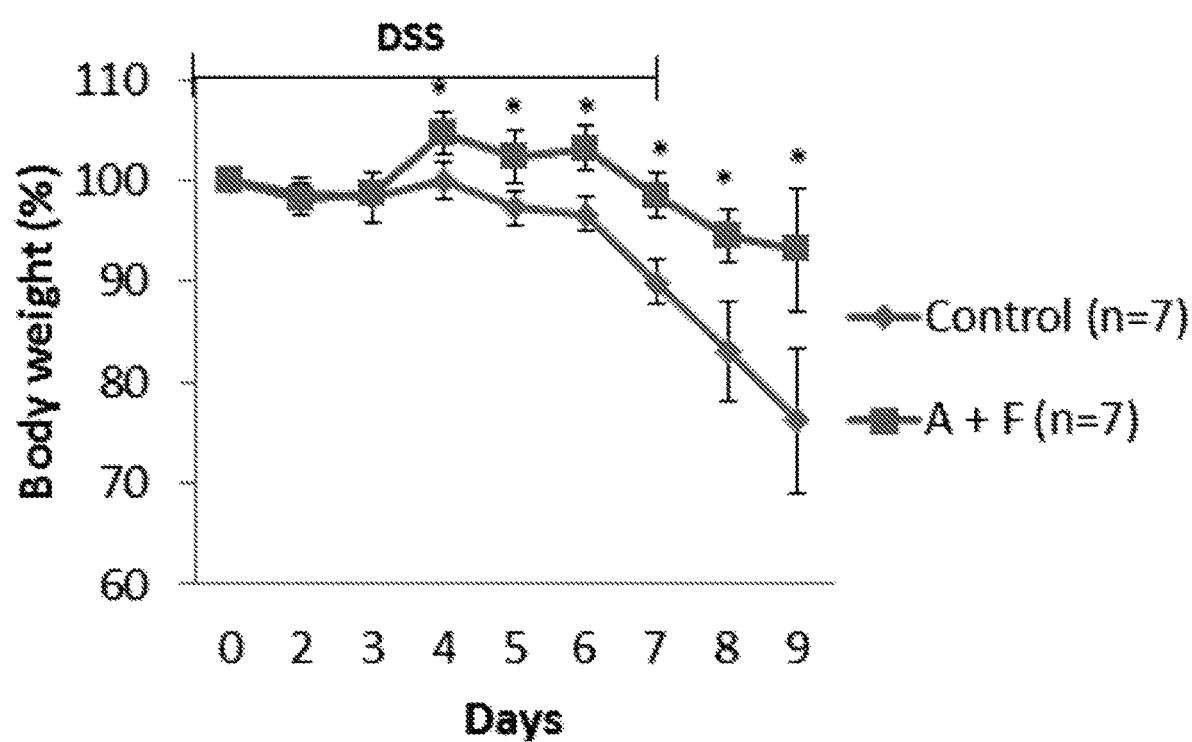
FIG. 20. Treatment with AF restored the body weight of mice with DSS-induced colitis. Colitis was induced in mice by the addition of 3% (wt/vol) DSS (MP Biochemicals, Solon, Ohio) in drinking water for 7 days. Mice were divided randomly into two experimental groups and received subcutaneous injections of saline or combination of AMD3100 and low-dose FK506 (A+F) form day 1 to day 9.

Treatment with AF restored the body weight of mice with DSS-induced colitis. 3% DSS was used for the DSS-colitis model. We observed that DSS at 3% or higher caused loss of colonic epithelial cells which is in agreement with previous reports. Mice were divided randomly into two experimental groups and received subcutaneous injections of saline or combination of AMD3100 and low-dose FK506 (AF) from day 1 to day 9. A significant weight loss was observed in control mice at day 9 after feeding with DSS. In contrast, the dual drug treatment restored the body weight of mice with DSS-induced colitis (FIG. 20).

Figure 21A:
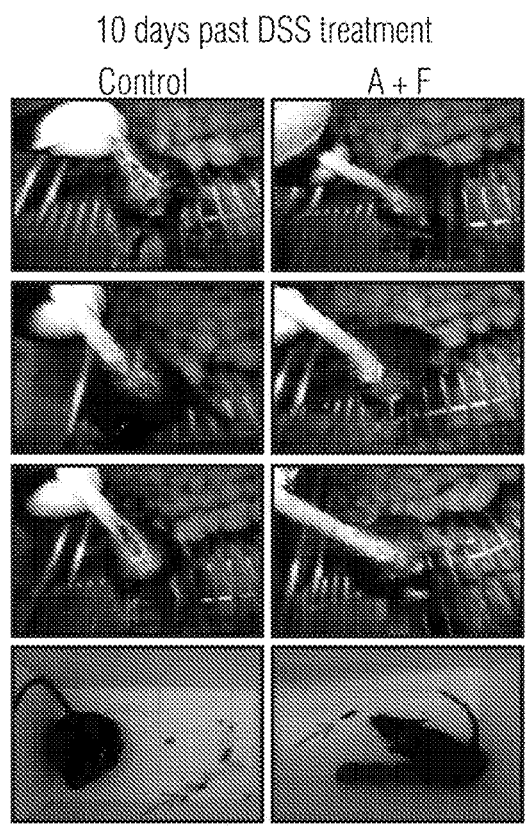
FIG. 21A-C. AF treatment decreased histologic severity of colonic inflammation in DSS-induced acute mouse colitis model.
Figure 21B:
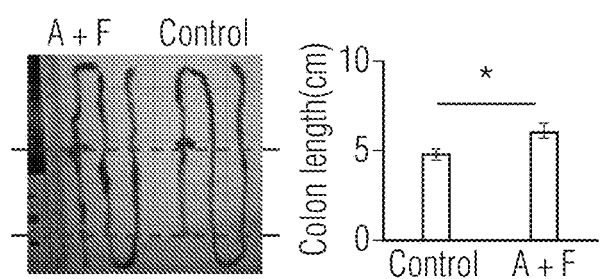
Figure 21C:
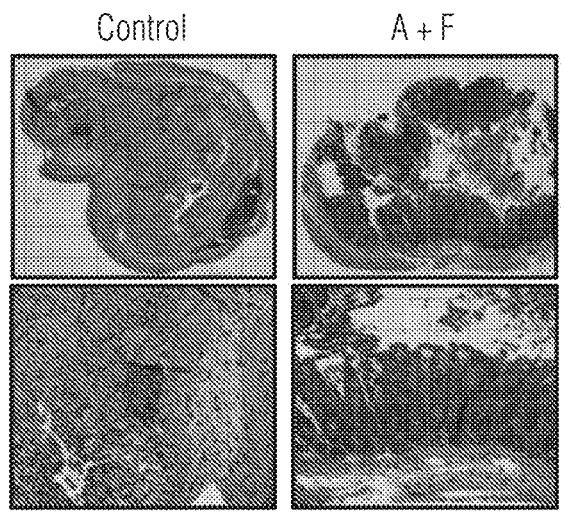

Administration of AF resulted in a significant improvement of the histology and disease activity index in DSS-induced acute mouse colitis model. Clinical progress in DSS-induced colitic mice was monitored. Bloody and loose stools, shorter and thickened colon and enlarged cecum were observed in saline treated mice compared with the dual drug treated mice at day 10 after beginning DSS feeding (FIGS. 21A and B). Histological analysis showed the loss or shortening of the crypts and apparent infiltration of inflammatory cells in lamina and muscularis mucosa in saline treated mice (FIG. 21C). In contrast, no significant intestinal epithelial surface damage or loss of surface epithelial cells was observed in DSS-induced colitis mice with dual drug treatment.

Figure 22:
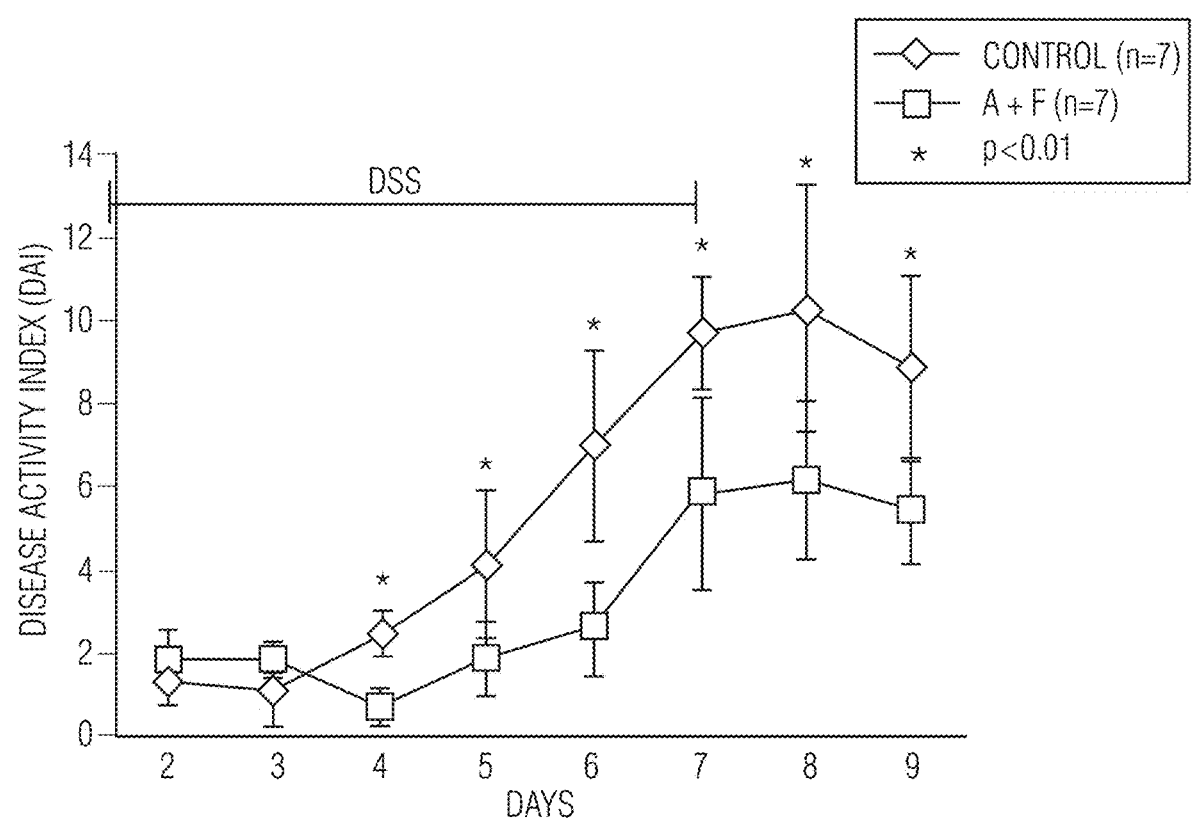
FIG. 22. Administration of AF resulted in a significant improvement of the disease activity index in DSS-induced acute mouse colitis model.

The progressive development of colitis is further demonstrated by the disease activity index (DAI). The DAI significantly increased at day 4 and reached the peak levels at day 8 after feeding with DSS in saline treated control animals (FIG. 22). Interestingly, the DAI were not increased until day 7 after feeding with DSS in mice with the dual drug treatment. The DAI were significantly higher in control animals compare to animals with the dual drug treatment at each time-point 4 days after DSS feeding (p<0.01).

Figure 23:
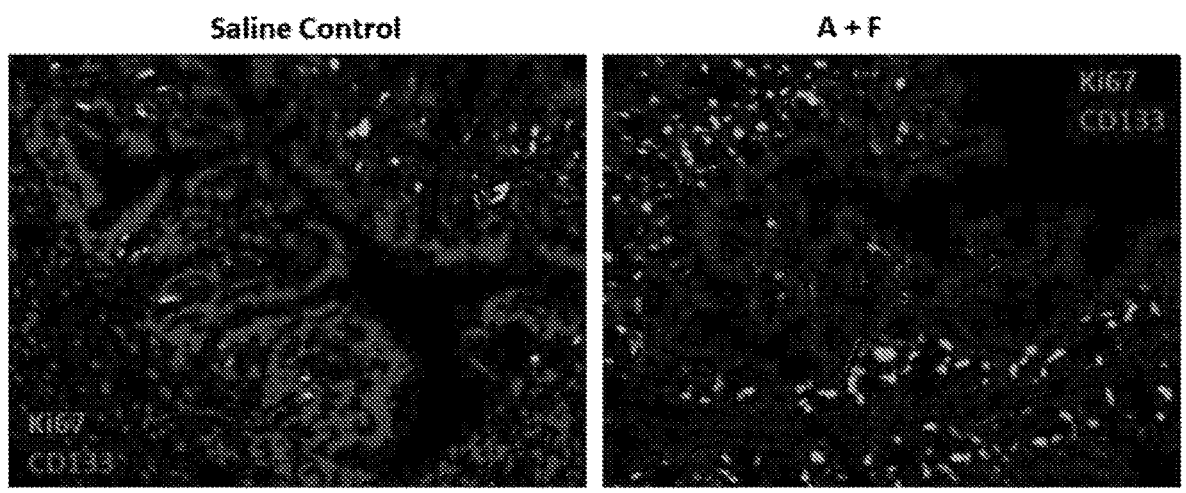
FIG. 23. AF treatment increase CD133 stem cells and improved regeneration of intestinal epithelium in DS-induced acute mouse colitis model. Immunofluorescence double staining of colon section. Ki67 stained green, CD133 sustained red. Representative photographs of n=3 individual samples per group.
Figure 25:
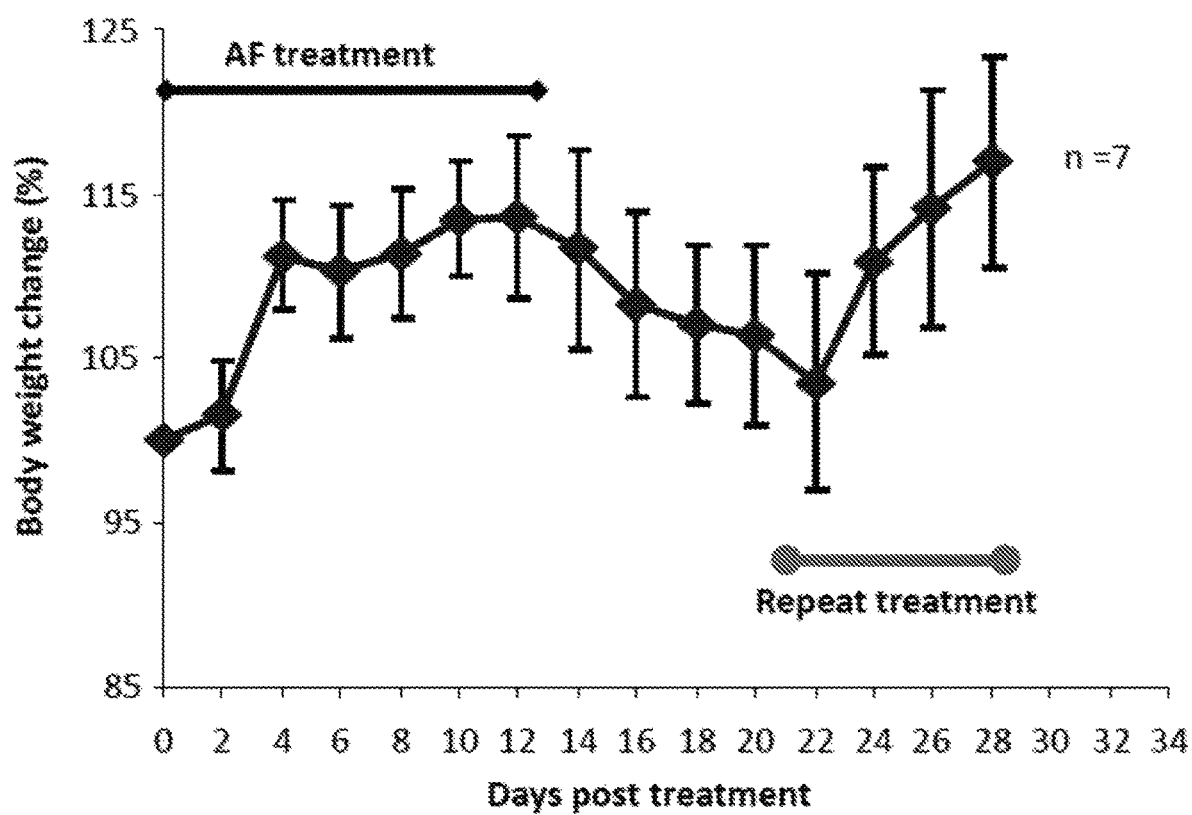
FIG. 25. Treatment with AF increased the body weight of IL-10-/- mice with colitis. The body weight was increased in IL-10-/- mice received subcutaneous injection of AF for 12 days, while the body weight was decreased 1 week after AF treatment. Repeat treatment restored the body weight.

AF treatment increased CD133 stem cells and improved regeneration of intestinal epithelium in DSS-induced acute mouse colitis model. CD133 stem cells and Ki67+ proliferating cells were measured in colon sections from saline control and AF treated mice by immunofluorescence double staining. A 7-day DSS treatment resulted in damages in the colonic crypt base (FIG. 21C) and reduced the number of $CD133^+$ stem cells (red) and Ki67+ proliferating cells (green) in the lower portion of the crypt (FIG. 23A). However, crypt histology, $CD133^+$ stem cells and Ki67+ proliferating cells were largely restored in mice with the dual drug treatment (FIG. 23B).

AF treatment decreased colonic inflammation in the IL-10-deficient murine model of IBD. Under the conditions present in our animal facility, C57BL/6 IL-10 deficient mice developed spontaneous colitis between 3 and 4 months of age. Animals with IBD were treated with AF (n=7) or saline for 3 weeks and sacrificed 1 week after treatment. Histologic examination of colon tissues from saline treated mice had moderate to severe colitis and epithelial hyperplasia with crypt branching (FIG. 24). AF treated mice had minimal inflammation.

Conclusion

Treatment with combination of AMD3100 and low-dose FK506 decreases the clinical and histologic severity of colonic inflammation and improved mucosal healing when administered to mice with dextran sulphate sodium (DSS)-induced colitis or IL-10 deficient mice with established colitis. Our findings offer a significant therapeutic approach for patients with IBD.

The invention claimed is:

1. A dosing regimen comprising:
   administering to a patient with inflammatory bowel disease a therapeutically effective amount of a stem cell mobilizer and an immunosuppressive agent,
   wherein the immunosuppressive agent is Tacrolimus,
   wherein the Tacrolimus is administered to the patient in an amount of 0.001 mg/kg to 0.009 mg/kg, and
   wherein the stem cell mobilizer is selected from the group consisting of AMD3100, AMD3465, TG-0054, G-CSF, GM-CSF, SDF-1, and SCF.

2. The dosing regimen of claim 1, wherein the stem cell mobilizer is a CXCR4 antagonist.

3. The dosing regimen of claim 1, wherein the stem cell mobilizer is AMD3100.

4. A dosing regimen comprising:
   administering to a patient with inflammatory bowel disease a therapeutically effective amount of an agent that mobilizes at least one of $CD34^+$ and $CD133^+$ stem cells and an immunosuppressive agent,
   wherein the immunosuppressive agent is Tacrolimus,
   wherein the Tacrolimus is administered to the patient in an amount of 0.001 mg/kg to 0.009 mg/kg, and wherein the agent that mobilizes at least one of CD34$^+$ and CD133$^+$ stem cells is selected from the group consisting of AMD3100, AMD3465, TG-0054, G-CSF, GM-CSF, SDF-1, and SCF.

5. The dosing regimen of claim 4, wherein the agent that mobilizes at least one of CD34$^+$ and CD133$^+$ stem cells is AMD3100.

\* \* \* \* \*